US012636513B2

(12) United States Patent
Hancock et al.

(10) Patent No.: US 12,636,513 B2
(45) Date of Patent: May 26, 2026

(54) DEVICE TO ELECTROMAGNETICALLY STIMULATE NEW ORGANIC CELL PROLIFERATION

(71) Applicant: EMDA LIMITED, Port Talbot (GB)

(72) Inventors: Colin Hancock, Nottinghamshire (GB);
Nigel John Clark, Shropshire (GB);
Tim Portass, Shropshire (GB)

(73) Assignee: EMDA LIMITED, Port Talbot (GB)

( * ) Notice: Subject to any disclaimer, the term of this patent is extended or adjusted under 35 U.S.C. 154(b) by 1038 days.

(21) Appl. No.: 17/417,864

(22) PCT Filed: Dec. 30, 2019

(86) PCT No.: PCT/EP2019/087172
§ 371 (c)(1),
(2) Date: Jun. 24, 2021

(87) PCT Pub. No.: WO2020/141165
PCT Pub. Date: Jul. 9, 2020

(65) Prior Publication Data
US 2022/0184408 A1     Jun. 16, 2022

(30) Foreign Application Priority Data
Dec. 31, 2018    (GB) ...................................... 1821315

(51) Int. Cl.
*A61N 2/00*          (2006.01)
*A61N 2/02*          (2006.01)
(Continued)

(52) U.S. Cl.
CPC .............. *A61N 2/004* (2013.01); *A61N 2/02* (2013.01); *B29C 64/386* (2017.08); *B33Y 50/00* (2014.12);
(Continued)

(58) Field of Classification Search
CPC ........ A61N 2/004; A61N 2/02; B29C 64/386; B33Y 50/00; B33Y 80/00; G06T 17/00; B29L 2031/753
(Continued)

(56) References Cited

U.S. PATENT DOCUMENTS

| 5,707,334 A | 1/1998 | Young |
| 2003/0158585 A1* | 8/2003 | Burnett .................. A61N 2/008 607/2 |

(Continued)

FOREIGN PATENT DOCUMENTS

| KR | 20140020682 A | 8/2014 |
| WO | 2013142339 A1 | 9/2013 |
| WO | 2017086820 A2 | 3/2017 |

OTHER PUBLICATIONS

English machine translation of KR20140020682.

*Primary Examiner* — Sunita Reddy
(74) *Attorney, Agent, or Firm* — Dickinson Wright PLLC; Andrew D. Dorisio

(57)          ABSTRACT

An apparatus for proliferation of organic tissue by exposure to electromagnetic field is disclosed that comprises an electromagnetic patch 101 comprising one or a plurality of electromagnetic coils 103 each generating an electromagnetic field; and a battery powered drive unit 102 which supplies signals to the electromagnetic coils for applying a particular dosage of electromagnetic field to a target tissue region. The electromagnetic patch 101 is specifically customised to an individual subject user and to an individual body portion and tissue region of said individual user. The drive signal sequence is individually tailored to the electromagnetic patch for delivering a particular dosage programme of electromagnetic field for the particular subject user.

11 Claims, 29 Drawing Sheets

(51) Int. Cl.

| | |
|---|---|
| *B29C 64/386* | (2017.01) |
| *B29L 31/00* | (2006.01) |
| *B33Y 50/00* | (2015.01) |
| *B33Y 80/00* | (2015.01) |
| *G06T 17/00* | (2006.01) |

(52) U.S. Cl.
CPC .............. *B33Y 80/00* (2014.12); *G06T 17/00*
(2013.01); *B29L 2031/753* (2013.01)

(58) Field of Classification Search
USPC ....................................................... 600/9–15
See application file for complete search history.

(56) References Cited

U.S. PATENT DOCUMENTS

| | | | |
|---|---|---|---|
| 2005/0236003 A1* | 10/2005 | Meader ................... | A61F 5/566 |
| | | | 128/848 |
| 2007/0203389 A1* | 8/2007 | Bergman ................. | A61N 1/40 |
| | | | 600/13 |
| 2009/0210032 A1* | 8/2009 | Beiski ................... | A61N 1/0548 |
| | | | 264/16 |
| 2011/0319947 A1* | 12/2011 | Chun ..................... | A61N 1/322 |
| | | | 607/2 |
| 2014/0135868 A1* | 5/2014 | Bashyam ............. | A61N 1/3601 |
| | | | 607/42 |
| 2014/0220509 A1* | 8/2014 | Vladila ............... | A61C 8/0006 |
| | | | 600/9 |
| 2014/0228619 A1* | 8/2014 | Moss ...................... | A61N 2/00 |
| | | | 600/12 |
| 2015/0032178 A1 | 1/2015 | Simon et al. | |
| 2018/0345032 A1 | 12/2018 | Lu | |
| 2019/0000594 A1* | 1/2019 | Vladila ................. | A61N 2/004 |

\* cited by examiner

TOOTH

1900

1902

1902

1900

Genotoxicity Time Limited Analysis

| Unit/Rig | | | | | Average | Hours/day |
|---|---|---|---|---|---|---|
| 5/5 8 7Hz 10 | AC 100 | 0.979 | 1.043 | 0.990 | 1.004 | 8 |
| 5/5 4 7Hz 9 | AC 100 | 0.968 | 0.980 | 0.994 | 0.981 | 4 |
| Const 8 7Hz 8 | AC 110 | 1.008 | 0.955 | 0.985 | 0.983 | 8 |
| Const 6 7Hz 7 | AC 110 | 1.027 | 1.004 | 0.998 | 1.010 | 6 |
| Const 4 7Hz 6 | AC 110 | 1.014 | 0.963 | 1.004 | 0.994 | 4 |
| 5/5 8 7.6Hz 5 | DC 130 | 1.049 | 1.011 | 0.984 | 1.015 | 8 |

Figure 36

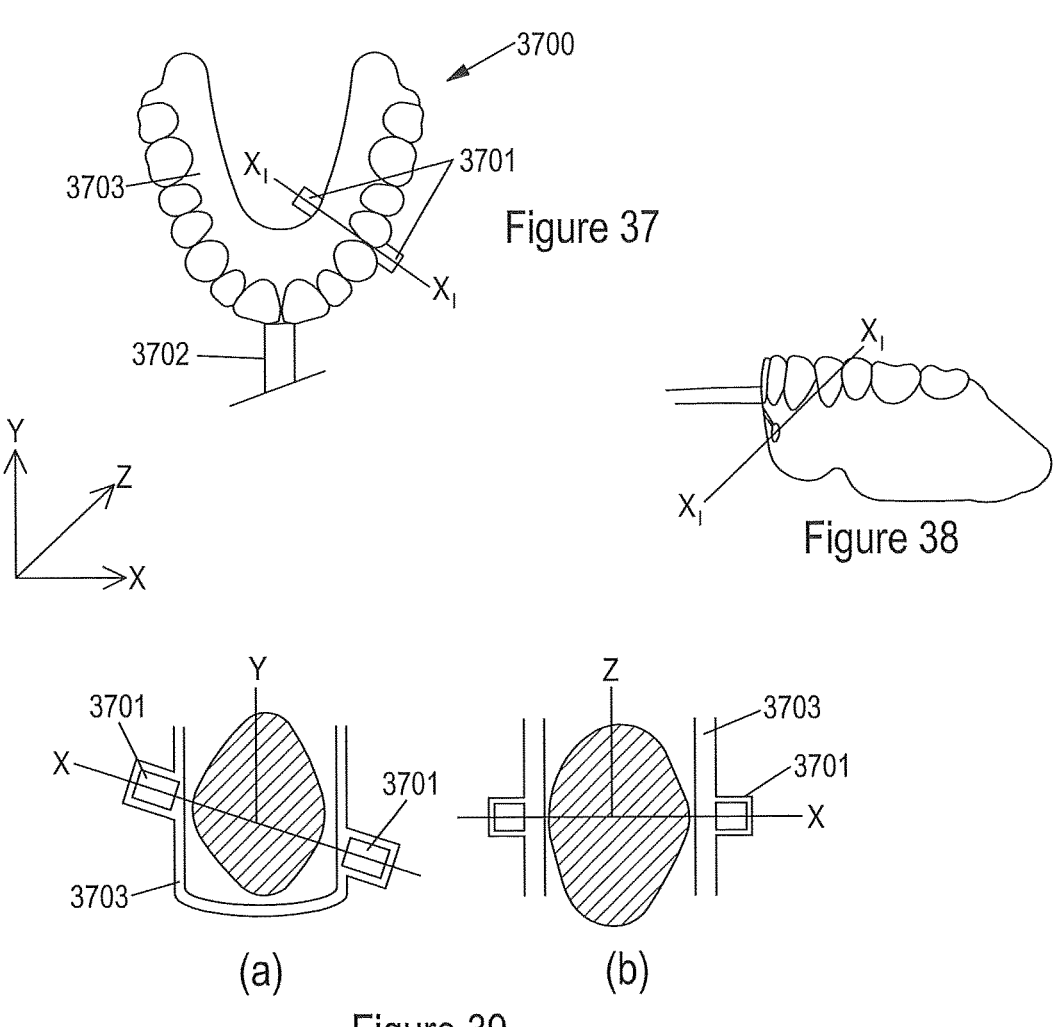
Figure 37
Figure 38
Figure 39
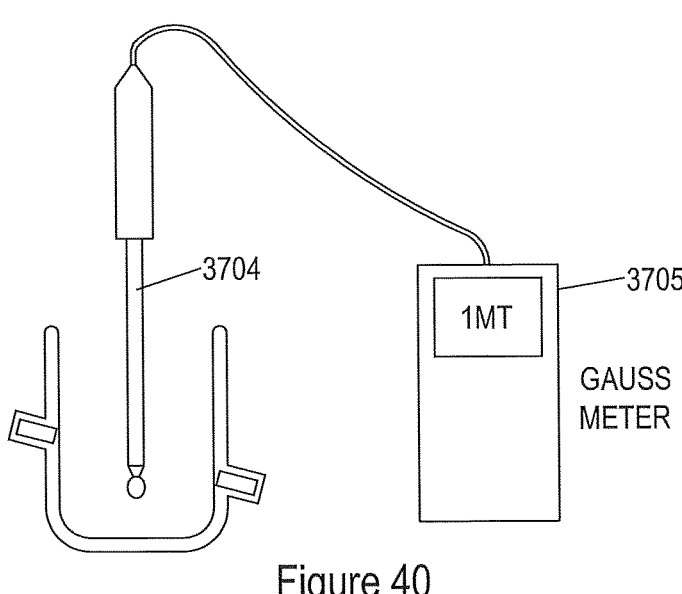
Figure 40

DEVICE TO ELECTROMAGNETICALLY STIMULATE NEW ORGANIC CELL PROLIFERATION

FIELD OF THE INVENTION

The present invention relates to electromagnetic stimulation of cells.

It is known to provide electromagnetic stimulation of cells or tissue to provide therapeutic and regenerative effect. Typically an electromagnetic coil is placed in the region of tissue to be treated and an electromagnetic field generated by the coil permeates the tissue. This is reported to have regenerative effect on the tissue.

Known examples of devices which apply cellular or tissue regenerative effects include dental patches shaped to fit a subject user's mouth. Examples are found in registered community design EM 003027663 "Bespoke electromagnetic dental stimulation applicator with encapsulated semi shielded coil (s)", and UK registered design GB 5000599.

However, in applying electromagnetic treatment to tissue over exposure to levels of electromagnetic radiation can also have damaging effect on cells of the tissue and a genotoxic effect, and so it is important that the overall exposure of the tissue to electromagnetic radiation is not so high as to cause permanent damage.

Known electromagnetic mouth inserts use coils which are large in relation to the available space in the mouth cavity. The large coils prevent localised specific application of an electromagnetic signal to the target cells, which means that higher power levels of electromagnetic signal need to be applied by the device to ensure that the signal required to generate cell growth or regeneration is received by the target tissue. However in applying higher signals through larger coils, neighboring healthy cells or areas of tissue may inadvertently be exposed to genotoxic levels of electromagnetic radiation.

Measuring the level of electromagnetic radiation experienced by a cell or tissue is not a straightforward task, as the individual cell or tissue may be inaccessible for direct measurement by means of measuring apparatus such as a Gauss meter or the like, and the electromagnetic field penetrates into the cell or tissue, where measuring instruments either cannot be inserted, or if inserted would be invasive to the area being treated.

In general the intensity of the electromagnetic signal decreases with distance from the coil according to an inverse square relationship. Placement of the coil in relation to the tissue to be treated is therefore an important parameter in determining the electromagnetic field strength experienced by the cell or tissue.

Further, known electromagnetic field emitting mouth inserts use analogue signal generators or microprocessors, which have a minimum increment accuracy of 0.25 mT. This limits the precision of the dosage of electromagnetic field exposure which can be applied.

Prior art electromagnetic field mouth inserts use high and potentially genotoxic levels of electromagnetic field to bridge the gap between the electromagnetic coil and the target cell/tissue region.

Other parameters which vary the effect of treatment of the cell or tissue include:

Power of the electrical signal to the electromagnetic coil, which affects magnetic field strength;

Frequency of oscillation of the electromagnetic signal;

Duration of exposure of the tissue to the electromagnetic signal; and

Periodicity (repetition period) of the treatment, whether daily, or at predetermined intervals.

In specific embodiments disclosed herein, electromagnetic coils having maximum dimensions of up to 7 mm are provided. The use of a relatively smaller coil means that the coil can be fitted in between two substrates to create an electromagnetic stimulation patch in which the placement of the coil can be made closer to a region of tissue to be exposed to the electromagnetic field created by the coil.

There is an advantage in using a relatively smaller coil in that a smaller coil can be placed more accurately adjacent and closer to the target region to be treated which in turn allows a lower absolute power or intensity levels of electromagnetic field to be used in order to achieve a same power density of electromagnetic field at the target region, compared to a larger coil which cannot be placed as close to the target cell or tissue region.

There is an advantage that a relatively smaller coil may be located closer and more accurately to a body region to be treated, compared to a relatively larger electromagnetic coil.

The relatively small dimensions of the coil also permits a more comfortable fit for the user in applications such as dental applications where the available space is restricted.

In various embodiments disclosed herein, a drive unit and power pack for providing an electric signal to an electromagnetic coil is prohibited from being connected to an external power supply, for example a mains alternating current (AC) power supply, or a mains power supply (AC/DC) or battery charger unit at the same time that an electromagnetic coil is connected to said drive unit.

SUMMARY OF THE INVENTION

According to a first aspect there is provided an apparatus for the electromagnetic stimulation of organic cells by an electromagnetic field, said apparatus comprising:

an electrostimulation device comprising at least one electromagnetic coil;

characterised in that;

said electrostimulation device is provided with a unique identifier device for identifying said electrostimulation device.

Preferably the electrostimulation device comprises a patch comprising at least one substrate.

Preferably the at least one electromagnetic coil is mounted within said at least one substrate; and said at least one electromagnetic coil is capable of generating an electromagnetic field strength of less than or equal to 5 mT at an outer surface of said patch at a drive frequency in the range 5.0 Hz to 8 Hz.

More particularly, the at least one electromagnetic coil is mounted within said at least one substrate; and said at least one electromagnetic coil is capable of generating an electromagnetic field strength of less than or equal to 5 mT at an outer surface of said patch at a drive frequency in the range 7.0 Hz to 7.6 Hz.

Preferably, said electromagnetic field generates a field strength of less than or equal to 5 mT at an outer surface of said patch at a distance beyond 1.5 to 3.0 mm from said electromagnetic coil at a drive frequency in the range 7.0 Hz to 7.6 Hz.

Preferably, said electromagnetic field generates a field strength of less than or equal to 1 mT at an outer surface of said patch at a distance beyond 1.5 to 3.0 mm from said electromagnetic coil at a drive frequency in the range 7.0 Hz to 7.6 Hz.

The electrostimulation device comprises a patch comprising a first substrate sheet and a second substrate sheet.

Said at least one electromagnetic coil is located between said first and second substrate sheets and said at least one electromagnetic coil is capable of generating an electromagnetic field;

said electromagnetic field having a field strength of less than or equal to 5 mT at a an outer surface of said patch at a drive frequency in the range 5.0 Hz to 8 Hz.

Said at least one electromagnetic coil generates a field strength of less than or equal to 5 mT at an outer surface of said patch at a drive frequency in the range 7.0 Hz to 7.6 Hz.

In an embodiment the electrostimulation device is ergonomically designed for dental wear.

Preferably, the electrostimulation device comprises a bespoke modified mouthguard. Advantageously, the mouthguard will be considered modified because it will incorporate an electromagnetic stimulation coil in combination with a custom-fit dental mouthguard allowing for optimised delivery of an electromagnetic field to a specific user.

Said unique identifier device comprises a device selected from the set:

an integrated circuit and/or a memory device storing a unique identifier data which uniquely identifies said electromagnetic stimulation device.

Said electromagnetic stimulation device comprises an electrical lead, wherein said unique identifier device is located at an opposite end of said lead to said at least one electromagnetic coil.

It is envisaged that said electromagnetic field generates a field strength of less than or equal to 1 mT at an outer surface of said electrostimulation device a drive frequency in the range 5.0 Hz to 8.0 Hz.

Said electromagnetic field generates a field strength of less than or equal to 1 mT at an outer surface of said electrostimulation device a drive frequency in the range 7.0 Hz to 7.6 Hz.

Said electromagnetic field is applied continuously for a period of 2 to 8 hours per day.

Said electromagnetic field is applied continuously for a period of 2, 4, 6 or 8 hours per day.

Said electromagnetic field is applied continuously for a period of 2 hours per day.

Said electromagnetic field is applied continuously for a period of 4 hours per day.

Said electromagnetic field is applied continuously for a period of 6 hours per day.

Said electromagnetic field is applied continuously for a period of 8 hours per day.

Said electromagnetic field is applied intermittently for a period of 2 to 8 hours per day.

Said electromagnetic field is applied intermittently for a period of 2, 4 or 6 hours per day.

Preferably, the electromagnetic field is applied intermittently for a period of 5 minutes then no electromagnetic field is applied for a period of 5 minutes, consecutively for a [the] designated treatment period of 2 to 8 hours per day.

Preferably, the electromagnetic field is applied intermittently for a period of 5 minutes then no electromagnetic field is applied for a period of 5 minutes, consecutively for a [the] designated treatment period of 2 hours per day.

Preferably, the electromagnetic field is applied intermittently for a period of 5 minutes then no electromagnetic field is applied for a period of 5 minutes, consecutively for a designated treatment period of 4 hours per day.

Preferably, the electromagnetic field is applied intermittently for a period of 5 minutes then no electromagnetic field is applied for a period of 5 minutes, consecutively for a designated treatment period of 6 hours per day. It will be understood that treatment programmes for individual subjects may operate on a daily, weekly or monthly or over any other specified treatment period with sub cycles within the overall treatment period and the treatment programmes being fully customisable and programmable. For example, the device may apply treatment for two, four or six hours per day, or any other time period between 0 and 24 hours within each day, as selected by medical practitioner or operator of the apparatus. The periods of operation may be intermittent or continuous within a daily 24 hour period. Intermittent can be any combination and duration of on/off cycles, e.g. 1 minute on/1 minute off, 5 minutes on/5 minutes off, 1 minute on/5 minutes off, 5 minutes on/3 minutes off etc.

Preferably said electromagnetic coil has a diameter of 3.9 mm to 6.0 mm and a height of 3.5 mm to 4.5 mm Preferably, the electromagnetic field is provided by a direct current.

Preferably, the electromagnetic field is provided by an alternating current.

Preferably the apparatus further comprises:

an electrical drive unit for generating a drive signal for powering said at least one electromagnetic coil, characterised in that;

said drive unit is provided with a recognition means for recognising said unique identifier device for identifying said electromagnetic stimulation apparatus; and said drive unit being operable to supply a drive signal to said at least one electromagnetic coil when said drive unit verifies said unique identifier device.

Preferably, said drive unit is operable to supply a drive signal to said at least one electro-magnetic coil when said drive unit verifies said unique identifier device.

Preferably, said drive unit is disabled from supplying a drive signal to said at least one electromagnetic coil when said drive unit does not verify said unique identifier device.

Preferably said unique identifier device comprises an integrated circuit and/or memory device storing a unique identifier data which uniquely identifies said electromagnetic stimulation apparatus.

Preferably, said apparatus further comprises:

means for preventing said drive unit from being connected to an external power supply when said electromagnetic coil is connected to said drive unit.

Said means for preventing said drive unit from being connected to an external power supply when said electromagnetic coil is connected to said drive unit comprises having only a single socket connector on said drive unit, which is used alternately for connection of an external power supply or for connection of one or more said electromagnetic coils, such that said power supply unit and a said electromagnetic coil cannot be connected to the same socket at the same time.

In a second aspect there is provided a method of electromagnetically stimulating organic cells, comprising the steps of:

applying an electromagnetic field via an electrostimulation device comprising at least one electromagnetic coil;

characterised in that;

said electrostimulation device is provided with a unique identifier device for identifying said electrostimulation device.

Preferably the electromagnetic field is applied by an electrostimulation device comprising a patch comprising at least one substrate.

Preferably the method generates an electromagnetic field strength of less than or equal to 5 mT at an outer surface of said patch at a drive frequency in the range 5.0 Hz to 8 Hz.

It is envisaged that the electromagnetic coil is mounted within said at least one substrate; and said at least one electromagnetic coil applies an electromagnetic field strength of less than or equal to 5 mT at an outer surface of said patch at a drive frequency in the range 7.0 Hz to 7.6 Hz.

Preferably the method includes applying an electromagnetic field via an electrostimulation device ergonomically designed for dental wear.

Preferably the method includes applying an electromagnetic field via an electrostimulation device which is a bespoke modified mouthguard.

Preferably the method involved applying an electromagnet field continuously for a period of 2 to 8 hours per day.

Preferably, the electromagnetic field is applied intermittently for a period of 5 minutes then no electromagnetic field is applied for a period of 5 minutes, consecutively for a [the] designated treatment period of 2 to 8 hours per day.

Preferably, the electromagnetic field is applied intermittently for a period of 5 minutes then no electromagnetic field is applied for a period of 5 minutes, consecutively for a designated treatment period of 2 hours per day.

Preferably, the electromagnetic field is applied intermittently for a period of 5 minutes then no electromagnetic field is applied for a period of 5 minutes, consecutively for a designated treatment period of 4 hours per day.

Preferably, the electromagnetic field is applied intermittently for a period of 5 minutes then no electromagnetic field is applied for a period of 5 minutes, consecutively for a [the] designated treatment period of 6 hours per day.

Preferably, the electromagnetic field is provided by a direct current.

Preferably, the electromagnetic field is provided by an alternating current.

Preferably the method further comprises the step of:

using an electrical drive unit to generating a drive signal for powering said at least one electromagnetic coil, characterised in that;

said drive unit is provided with a recognition means for recognising said unique identifier device for identifying said electromagnetic stimulation apparatus; and said drive unit being operable to supply a drive signal to said at least one electromagnetic coil when said drive unit verifies said unique identifier device.

Preferably, said drive unit is operable to supply a drive signal to said at least one electro-magnetic coil when said drive unit verifies said unique identifier device.

Preferably, said drive unit is disabled from supplying a drive signal to said at least one electromagnetic coil when said drive unit does not verify said unique identifier device.

Preferably said unique identifier device comprises an integrated circuit and/or memory device storing a unique identifier data which uniquely identifies said electromagnetic stimulation apparatus.

In a third aspect there is provided a drive unit for an electromagnetic stimulation device, said electromagnetic stimulation device comprising a substrate and at least one electromagnetic coil, said drive unit comprising:

a power storage device;

a microprocessor device;

a power circuit for providing drive current to said at least one electromagnetic coil;

connection means for connecting said drive unit to a said at least one electromagnetic stimulation device; and means for receiving and storing a set of signal data for implementing a programme comprising a series of one or more drive signals applied to said at least one electromagnetic stimulation device.

Preferably, said means for receiving and storing a set of drive signal data comprises:

a communications port; and a memory device and/or a data storage device for storing said set of signal data.

Preferably, the drive unit comprises means for uniquely identifying an individual electromagnetic stimulation device from a plurality of said electromagnetic stimulation devices.

Preferably, the drive unit comprises means for receiving an external power input for charging said power storage device, and connection means for connecting said drive unit to a said electromagnetic stimulation device, said connection means being configured such that connection of said drive unit to said external power input and to said electromagnetic stimulation device at the same time are mutually exclusive so that the external power input cannot be connected to the drive unit at the same time that the drive unit is connected to said electromagnetic stimulation device.

In a fourth aspect there is provided a method for creating a design of a bespoke apparatus for an individual subject for the electromagnetic stimulation of organic cells, said method comprising:

identifying a target region within a body region of said individual subject, which is to be subjected to electromagnetic stimulation;

creating a data map of said body region of said individual subject;

determining a required electromagnetic field strength in said target region;

using said data map of said body region to create a 3-dimensional data map for an electrostimulation device which closely fits said body region; and positioning at least one coil within said 3-dimensional map for said electrostimulation device so as to deliver a said required electromagnetic field to said target region.

Preferably, the method further comprises creating a set of signal data for driving said electrostimulation patch with a signal which produces said required electromagnetic field strength in said target region.

Preferably, the method further comprises determining an electric field strength throughout the whole of said body region; and determining whether said electric field strength falls above a genotoxic level of electric field strength at any position within said body region; and if said electric field strength falls above said genotoxic level at any position within said body region, selecting a different alternative electromagnetic coil which produces a lower electromagnetic field strength.

Said data map of said body region comprises a 3-dimensional data map.

Said process of identifying a target region comprises creating a 3-dimensional data map of said target region.

Said process of positioning said at least one coil comprises determining an optimum position of said at least one coil in 3-dimensional space relative to said body portion.

Said process of positioning said at least one coil comprises determining an optimum orientation of a main plane of the windings of said at least one in 3-dimensional space relative to said target region.

Preferably, the method further comprises manufacturing an electromagnetic stimulation apparatus according to said 3-dimensional electrostimulation patch data.

According to a firth aspect there is provided an apparatus for promoting the proliferation of organic cells by electromagnetic stimulation, said apparatus comprising at least one electromagnetic coil for generating an electromagnetic field; and an electrical drive unit for generating a drive current for powering said at least one electromagnetic coil, said apparatus characterised by comprising: means for preventing said drive unit from being connected to an external power supply when said electromagnetic coil is connected to said drive unit.

Preferably, said means for preventing said drive unit from being connected to an external power supply when said electromagnetic coil is connected to said drive unit comprises having only a single socket connector on said drive unit, which is used alternately for connection of an external power supply or for connection of one or more said electromagnetic coils, such that said power supply unit and a said electromagnetic coil cannot be connected to the same socket at the same time.

In a sixth aspect there is provided a method of manufacture of an apparatus for the electromagnetic stimulation of organic cells by application of an electromagnetic field, said method comprising:

generating data describing physical characteristics of a required electrostimulation device;

said data comprising:

three-dimensional map data specifying a 3-dimensional shape of said electrostimulation device;

substrate material data describing at least one substrate material type for manufacture of a body of said electrostimulation device;

data describing the number, type and positions of one or more individual coils to be incorporated into said body of the electrostimulation device; and manufacturing an electrostimulation device according to said data.

Said method of manufacturing comprises printing said body according to said three-dimensional map data using a 3-dimensional printer.

Said data further comprises identification means for identifying said electromagnetic stimulation apparatus.

Said identification device data comprises data describing a type of identification means, comprising an integrated circuit comprising a unique identifier data which uniquely identifies said electromagnetic stimulation apparatus.

Said method of manufacturing electromagnetic stimulation apparatus further comprises incorporating at least one identification device into said electrostimulation device.

Said method of manufacturing further comprising:

individual electrostimulation device identification data to identify an individual electrostimulation device once manufactured; and said method of manufacture comprises incorporating an identification device into said electrostimulation device; and incorporating said device identification data into said identification device.

Said method of manufacturing said data describing the number, type and positions of one or more individual coils to be incorporated into said body of the electrostimulation device comprises:

reading electromagnetic field measurement data determined from measurements made experimentally from an electromagnetic coil positioned adjacent a physical model of a body portion of said subject user;

comparing said experimentally determined electromagnetic field measurement data with said three-dimensional map data of said shape of said electrostimulation device;

reading electromagnetic field strength data relating to one or more selected electromagnetic coil types from pre-stored data in a database;

comparing said experimentally determined electromagnetic field measurement data from said physical model of said subject user with said pre-stored electromagnetic field strength data from said database; and selecting an individual electromagnetic coil type which generates an electromagnetic field strength below a genotoxic level throughout the whole of a 3 dimensional region corresponding to said experimentally determined electromagnetic field measurement data.

Said method further comprising selecting a position of a said selected individual electromagnetic coil within said 3-dimensional map data specifying said 3 dimensional shape for the electrostimulation device, at which said selected electromagnetic coil generates an electromagnetic field strength below a genotoxic level through the whole of said 3 dimensional region corresponding to said experimentally determined electromagnetic field measurement data.

Said method further comprising selecting positions for two or more selected individual electromagnetic coils within said 3 dimensional map data specifying said 3 dimensional shape of said electrostimulation device, at which said selected electromagnetic coils collectively generate an electromagnetic field strength below a genotoxic level throughout the whole of said 3 dimensional region corresponding to said experimentally determined electromagnetic field measurement data.

Said method of manufacturing wherein said process of generating data describing the number, type and position of one or more individual coils comprises determining a cell type of a target region of the body portion of a subject; and selecting a coil type from set of one or more coil types which have been pre-determined to generate electromagnetic field strengths which are non-genotoxic for said determined cell type.

In a seventh aspect a method for providing a set of drive signal data for a drive unit to supply drive signals to an electrostimulation device is provided, said method comprising:

creating a data map of a body region of said individual subject;

identifying a target region within said body region which is to be subjected to electromagnetic stimulation;

determining a required electromagnetic field strength in said target region;

determining a position of said at least one electromagnetic field generating coil in relation to said target region at which said at least one electromagnetic coil provides a said required electromagnetic field strength in said target region; and determining a drive signal which delivers said required electromagnetic field strength in said target region.

Said method wherein said step of determining a drive signal which delivers said required electromagnetic field strength in said target region may further comprise selecting a digitally synthesised waveform from a pre-stored library of digitally synthesised waveforms.

Said method wherein said step of determining a drive signal which delivers said required electromagnetic field strength in said target region may further comprise digitally synthesising a bespoke waveform envelope which produces said required electromagnetic field strength in said target region.

Said method wherein said step of determining a drive signal which delivers said required electromagnetic field strength in said target region may further comprise generating a computerised 3 dimensional model of electromagnetic field strength produced by known coil; overlaying said computerised 3-dimensional model of electromagnetic field strength with a three-dimensional data map of a target region of a body portion which is to be subjected to said electromagnetic field; applying successively one or a plurality of individual pre-stored drive signal waveforms to a computer simulation of said known electromagnetic coil to determine a simulated electromagnetic field strength produced by each of said successively applied drive signal waveform; and selecting a said pre-stored drive signal waveform which produces a required electromagnetic field strength throughout the whole of said target region.

Said method wherein said selected drive signal waveform is selected so that the electromagnetic field strength is below a genotoxic level throughout the whole of said target region.

Other aspects are as set out in the claims herein, which are incorporated in the description herein by way of reference.

BRIEF DESCRIPTION OF THE DRAWINGS

For a better understanding of the invention and to show how the same may be carried into effect, there will now be described by way of example only, specific embodiments, methods and processes according to the present invention with reference to the accompanying drawings in which.

Figure 29:
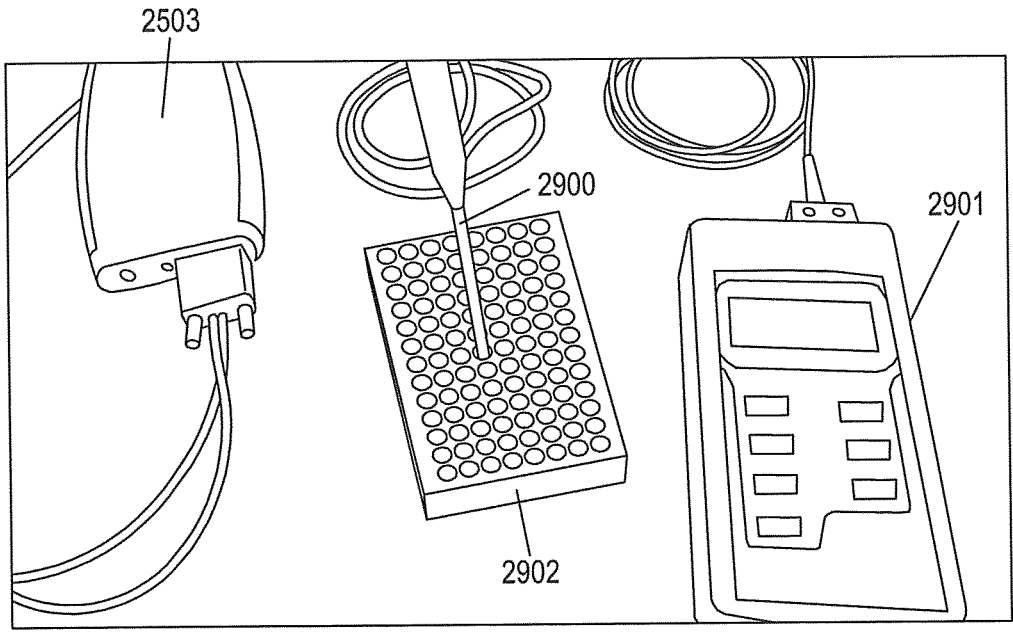
Figure 30:
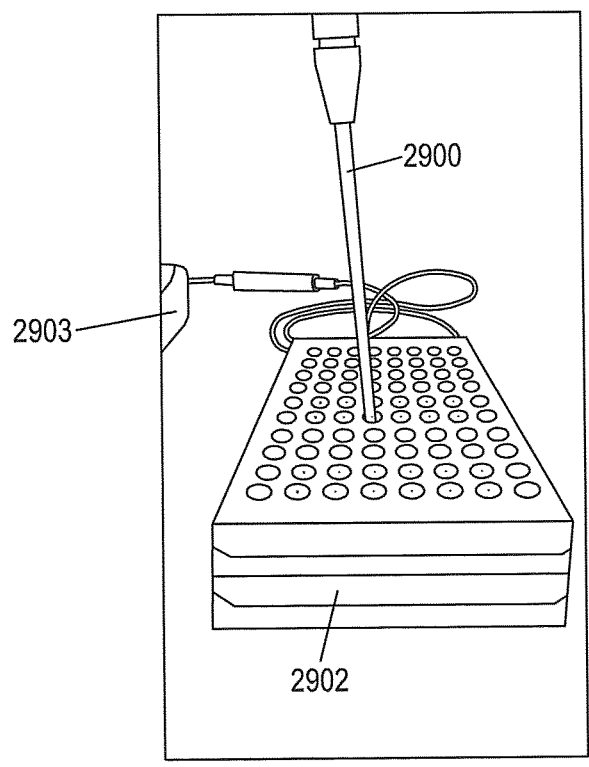
Figure 31:
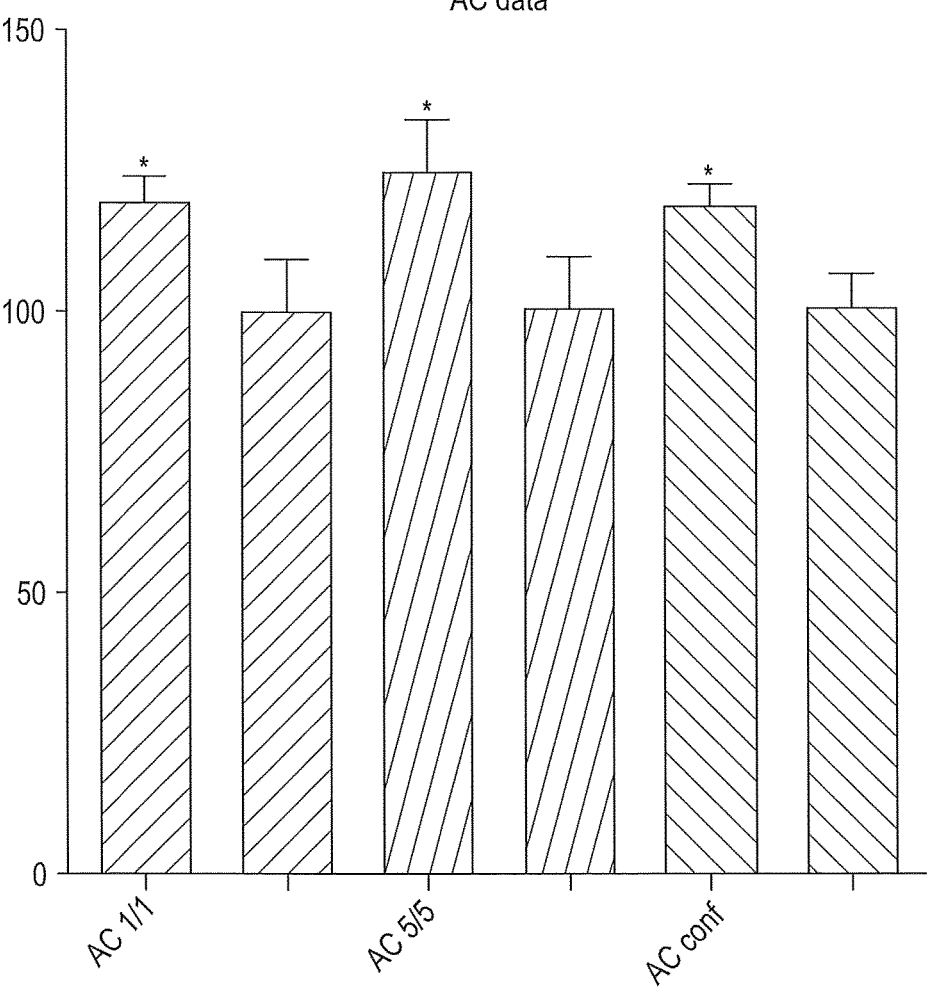
Figure 32:
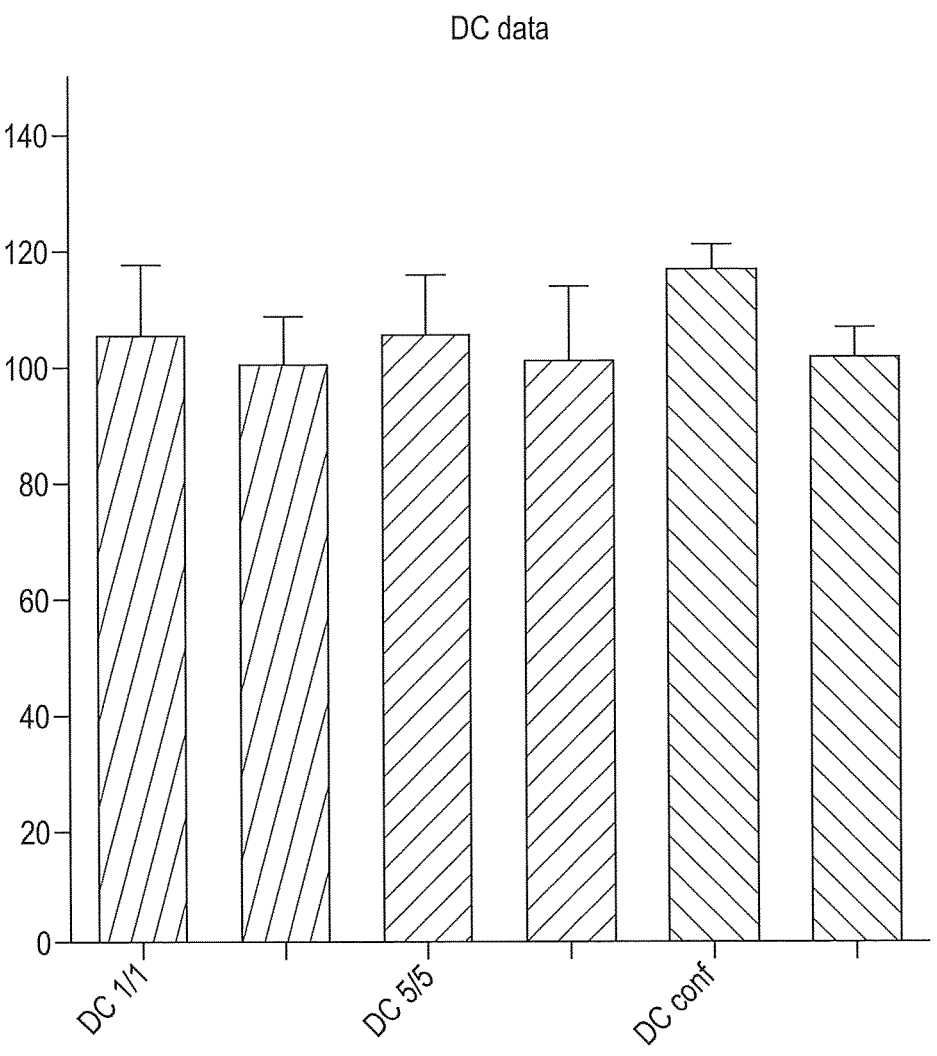
Figure 33:
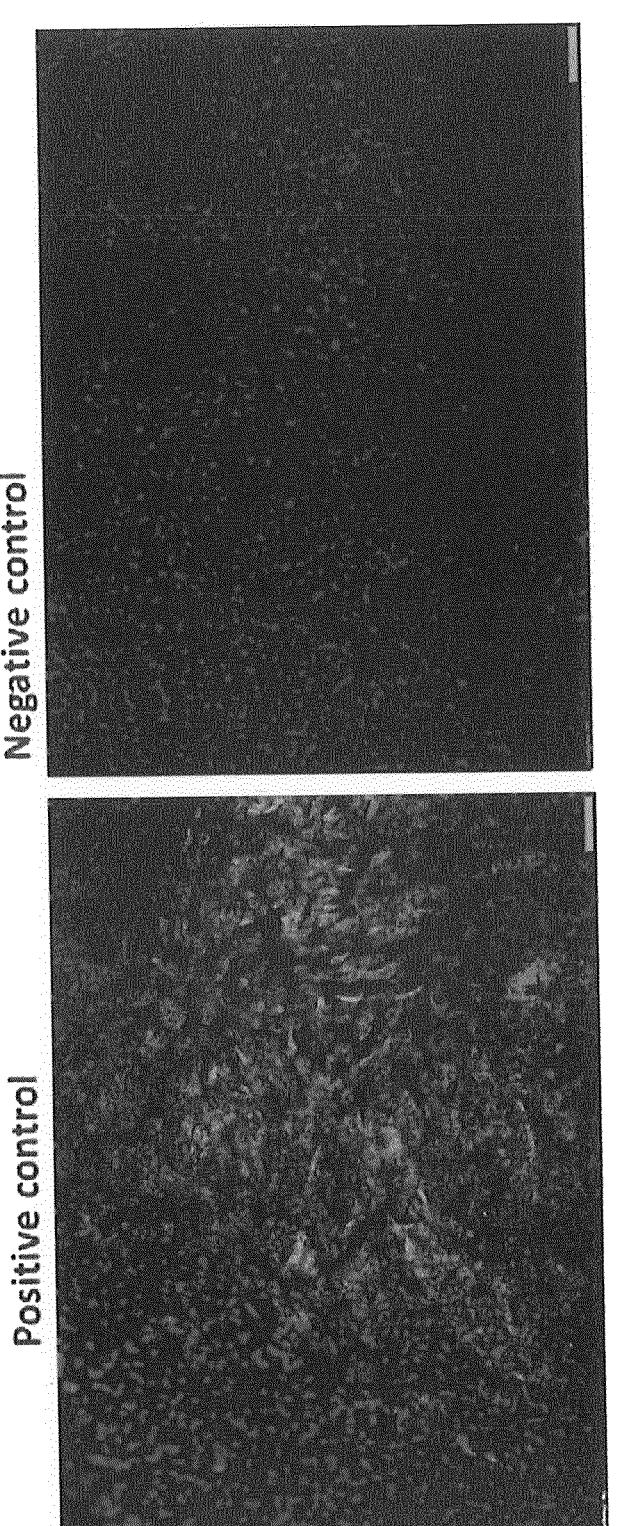
Figure 34:
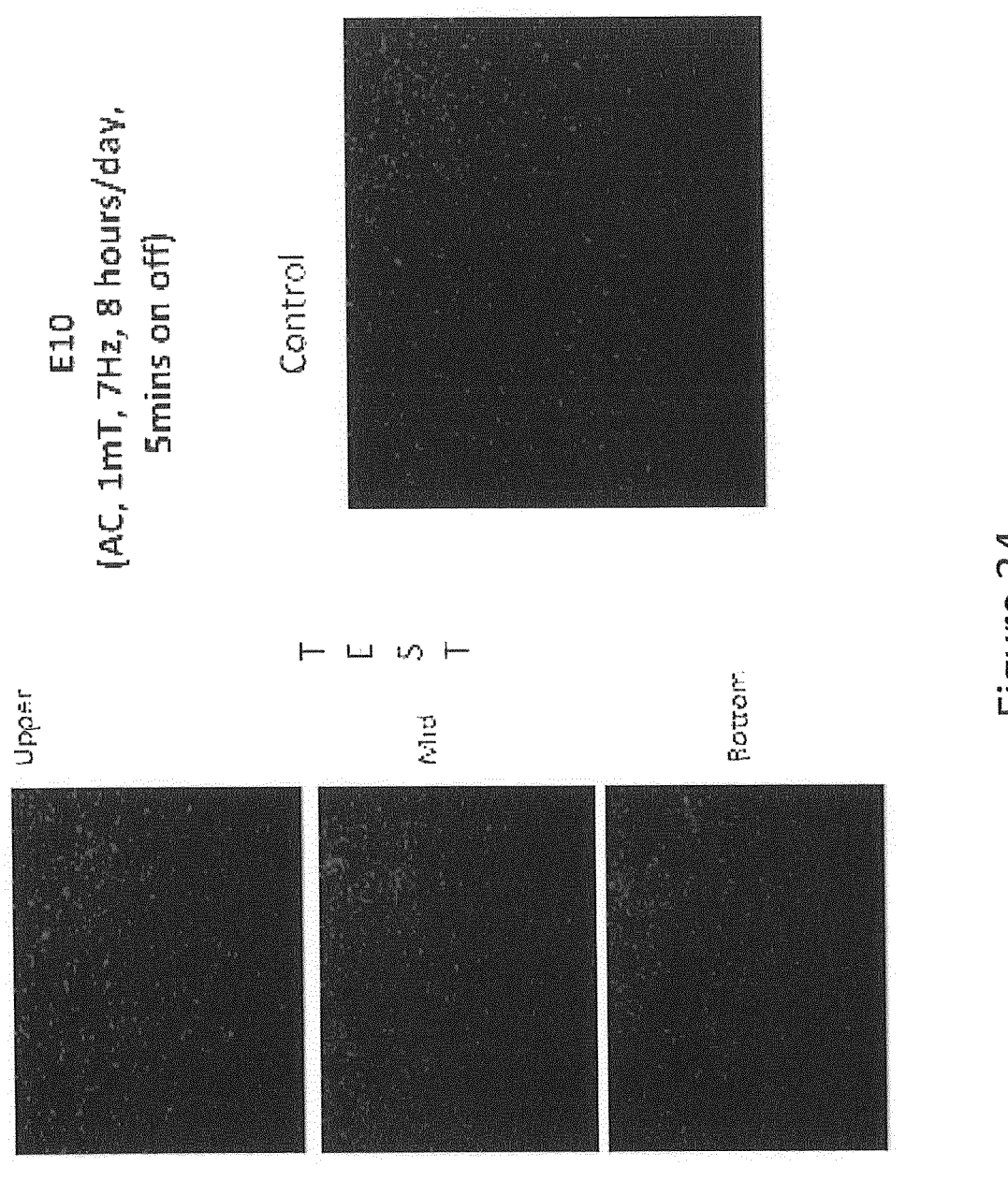
Figure 35:
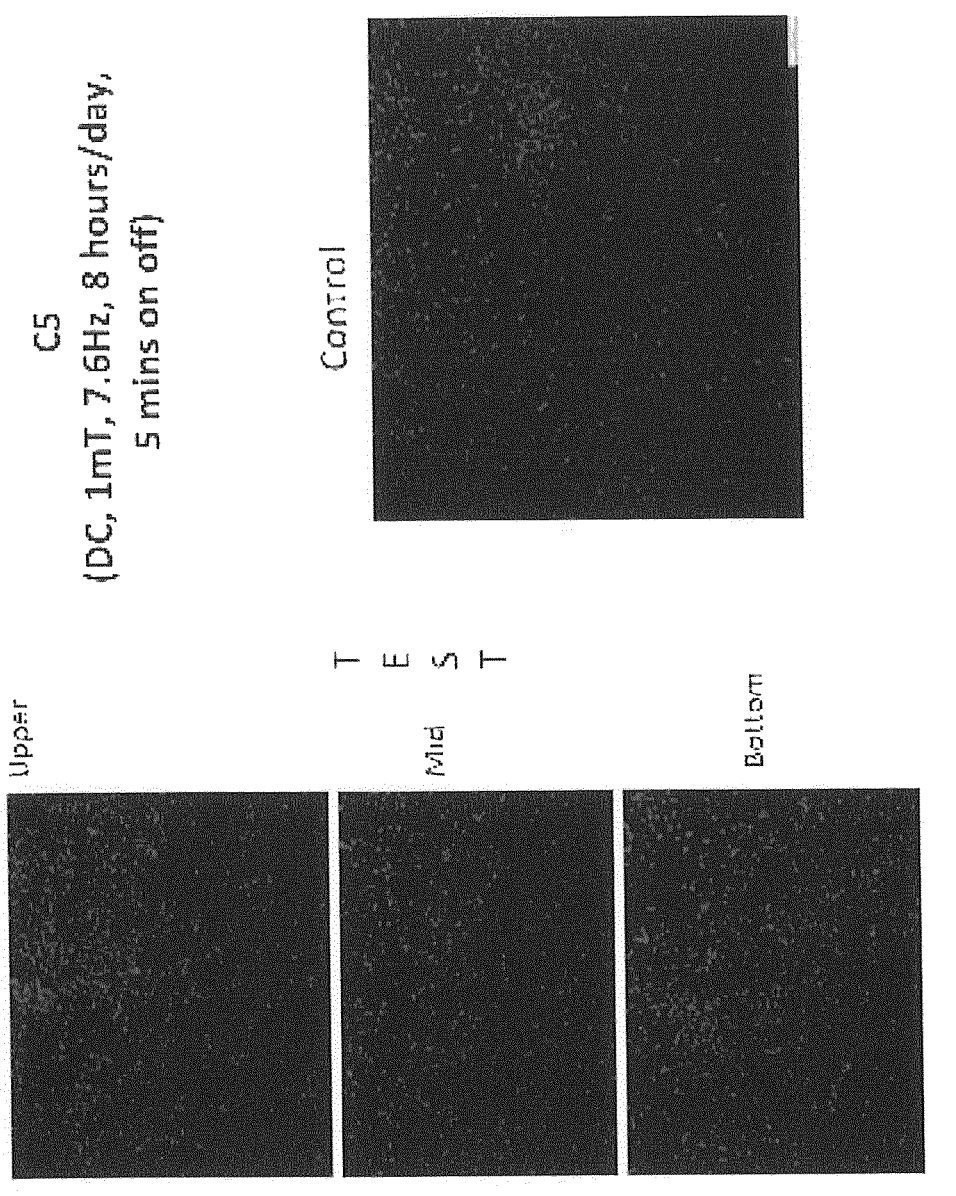

Figure herein 28 illustrates schematically a view from above of a 96 well plate layout used for in vitro cell proliferation assays in which cell proliferation is measured under conditions of electromagnetic stimulation at various different frequencies in comparison with a control sample;

FIGS. 29 and 30 herein illustrate schematically respective views of the test rig used for in vitro cell proliferation assays in which cell proliferation is measured under conditions of electromagnetic stimulation at various different frequencies in comparison with a control sample;

FIG. 31 herein illustrates schematically a plot of percentage cell proliferation for cells exposed to AC electromagnetic stimulation at different duty cycles on 1/1 and 5/5 at a continuous signal;

FIG. 32 herein illustrates schematically a plot of percentage cell proliferation for cells exposed to DC electromagnetic stimulation at frequencies on different duty cycles on 1/1 and 5/5 at a continuous signal;

FIG. 33 herein illustrates schematically control slides viewed microscopically at using a fluorescence microscope, to show the genotoxic effects upon cells exposed to AC or DC electromagnetic stimulation at differing frequencies. The positive control is etoposide 2 positive and the negative control is gingiva fibroblast primary isolated cells;

FIG. 34 herein illustrates schematically determination of the safe conditions for AC electromagnetic stimulation at 1 mT, 7 Hz, 8 hours/day 5 minutes on/off;

FIG. 35 herein illustrates schematically determination of the safe conditions for DC electromagnetic stimulation at 1 mT, 7.6 Hz, 8 hours/day 5 minutes on/off;

FIG. 36 herein illustrates a table of results of a time-limited assessment trial to better reflect the conditions which would apply in the clinical setting having treatment intervals of four, six or eight hours per day;

FIG. 37 herein illustrates schematically in plan view a treatment patch having a pair of diametrically opposed electromagnetic coils placed either side of an individual tooth;

FIG. 38 herein illustrates schematically in view from one side the treatment patch of FIG. 37;

FIGS. 39*a* and 39*b* respectively illustrate schematically parts of the treatment patch of FIG. 38 in view along a main channel of the treatment patch as shown in FIG. 39*a*, and in plan view as shown in FIG. 39*b;*

FIG. 40 illustrates schematically a Gauss meter attached to a probe for measuring magnetic field strength at positions between the two electro-magnetic coils of the treatment patch of FIG. 39*a*.

DETAILED DESCRIPTION OF THE EMBODIMENTS

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

In this specification, the term "subject" or "subject user" is used to mean any animal or human subject having cellular structure, and is used interchangeably with the term "patient" to mean the same thing.

In the specification, the term "treatment programme" is used to describe a set or sequence of electromagnetic signals which may vary in signal strength, signal duration, oscillation period, pulse width, duty cycle and repetition of sequences of series or sets of pulses or oscillations as applied to an anatomical region of a subject. References to drive signals for delivering a "treatment programme" are to be construed accordingly.

In the specification, a course of treatment (which may also be referred to as a "treatment plan") may comprise one or more treatment programmes as prescribed or devised to suit a particular subject, for treatment of a particular region of tissue of said subject.

In the attached drawings, to assist clarity and understanding, like parts, features or components are given like reference numerals from drawing to drawing.

Specific embodiments and methods disclosed herein relate to a system to promote the proliferation of organic cells in human or animal bodies.

Embodiments disclosed herein aim to provide a method and apparatus for electromagnetically stimulating organic cell proliferation in human and/or animal subjects, by spatially arranging one or more individual electromagnetic coils to be positioned as close as possible to a target region of tissue to be regenerated, and by providing that an electromagnetic field strength present at an outer surface of a body portion containing said target tissue region is below a level which causes genotoxic effect, preferably at or below 1.0 mT.

The system comprises an electromagnetic patch which uses a medium to hold wire coils close to or inside the human or animal body. An electromagnetic signal is applied via those wire coils. The characteristics of the signal is specific to an individual subject user or patient.

The signal is generated at a particular frequency and a particular power using a set of digitally generated drive signals. There may be more than one coil in each electromagnetic patch and each electromagnetic coil may be driven with a corresponding respective separate set of drive signals. The drive signals are digitally generated and are configured to deliver a required electromagnetic field dosage treatment programme to a specific tissue region at a specific body portion of the human or animal subject.

The characteristics of the signal are patient-specific. Patient specific parameters are determined by a clinician examining the subject user or patient and determining an area of treatment. For example for dental treatment the area treatment is determined by reference to normal dental charting. The clinician uploads all relevant medical and/or dental data to a remote server computer.

At a remote server computer there are stored predetermined data obtained through experimentation on gingival cells in laboratory experiments which determines what a safe level of electromagnetic field is for a particular type of cell. This data is used to generate a configuration and design of an electromagnetic patch together with the drive signal and/or drive signal sequence for powering the electromagnetic patch, which can be fitted to a particular body portion of a subject user in order to treat a particular defined target tissue region of that subject user which maintains electromagnetic field levels within safe non-genotoxic levels for that particular application on that particular subject user.

Those patient-specific parameters are obtained from a database held on a remote computer where connection is made according to communications links so that a set of digitally generated drive signals can be sent from a remote location to a local drive unit and electromagnetic treatment device in the form of an electromagnetic patch to deliver a programme of treatment specific to an individual subject user.

The drive signal may be either AC or DC. The drive signal comprises an overall envelope which gives the overall wave form, for example a sinusoidal wave form. The waveform is digitally synthesised from a larger number of smaller individual digital pulses, typically between 1000 and 10,000 individual pulses making up one period P of the overall wave form. In principle, any arbitrary shape of digital pulse may be specified or used which is capable of being digitally synthesised and the pulse shape is not restricted to the specific examples described herein.

Using patient specific parameters which are obtained by measurement by a clinician or medical personnel, a set of one or more drive signals and a drive signal sequence are generated which are specific to that particular subject user or patient. The drive signals and drive signal sequence are digitally generated at a remote computer. The drive signal and drive signal sequence can be sent from the remote computer to the drive unit to configure the drive unit to supply the patient specific drive signal and drive signal sequence which represents a programme of electromagnetic field treatment created specifically for that subject user or patient.

The apparatus and system include for verification of a drive signal and drive signal sequence specific to an individual subject user. This is achieved by providing an electromagnetic patch device comprising one or more electromagnetic coils, the electromagnetic patch being manufactured with an identification device. The unique hardware identifier which is built into the applicator is recorded into software which is stored in a database. A drive unit which drives the electromagnetic patch identifies the electromagnetic patch using the identification device in order to verify that the electromagnetic patch is matched to the drive signal and/or drive sequence stored in the drive unit.

Physiological data provided by the dental surgeon is entered into a software application which stores in a database patient-specific and treatment-specific data. The data is combined in software with the data provided at the time of manufacture to calculate the operating characteristics of the device.

In order to achieve optimised results, the electromagnetic field strength needs to be high enough in order to stimulate cell proliferation, but should be below an electromagnetic field strength which produces genotoxic effect. In the best mode embodiments, the electromagnetic field strength at an outer surface of the electromagnetic patch which lies adjacent and/or in contact with an outer surface of a body part, for example a tooth or gum has an electromagnetic field strength of no greater than 5 mT, preferably less than 1.5 mT, and suitably less than 1 mT. The electromagnetic field strength generated by an individual electromagnetic coil and/or combination electromagnetic coils generating a localised electromagnetic field is designed such that the electromagnetic field strength at the outer surface of the electromagnetic patch is preferably less than 1.5 mT and suitably, less than 1 mT.

When the signal generator is configured for a particular patient and treatment programme, the data is specific to the unique hardware identifier built into the applicator and a course of treatment prescribed or set by the dental surgeon. Thus, a high threshold of safety check is included in the apparatus ensuring that only the correct applicator is connected to the power supply device to provide the designated treatment to a patient. In the event the wrong applicator is selected the device will not be operable as the software controlling the power supply would not recognize an incorrect unique hardware identifier. This safety check prevents the wrong device being used on the wrong patient or the wrong treatment course of treatment being initiated, i.e. it reduced user error.

Figure 1:
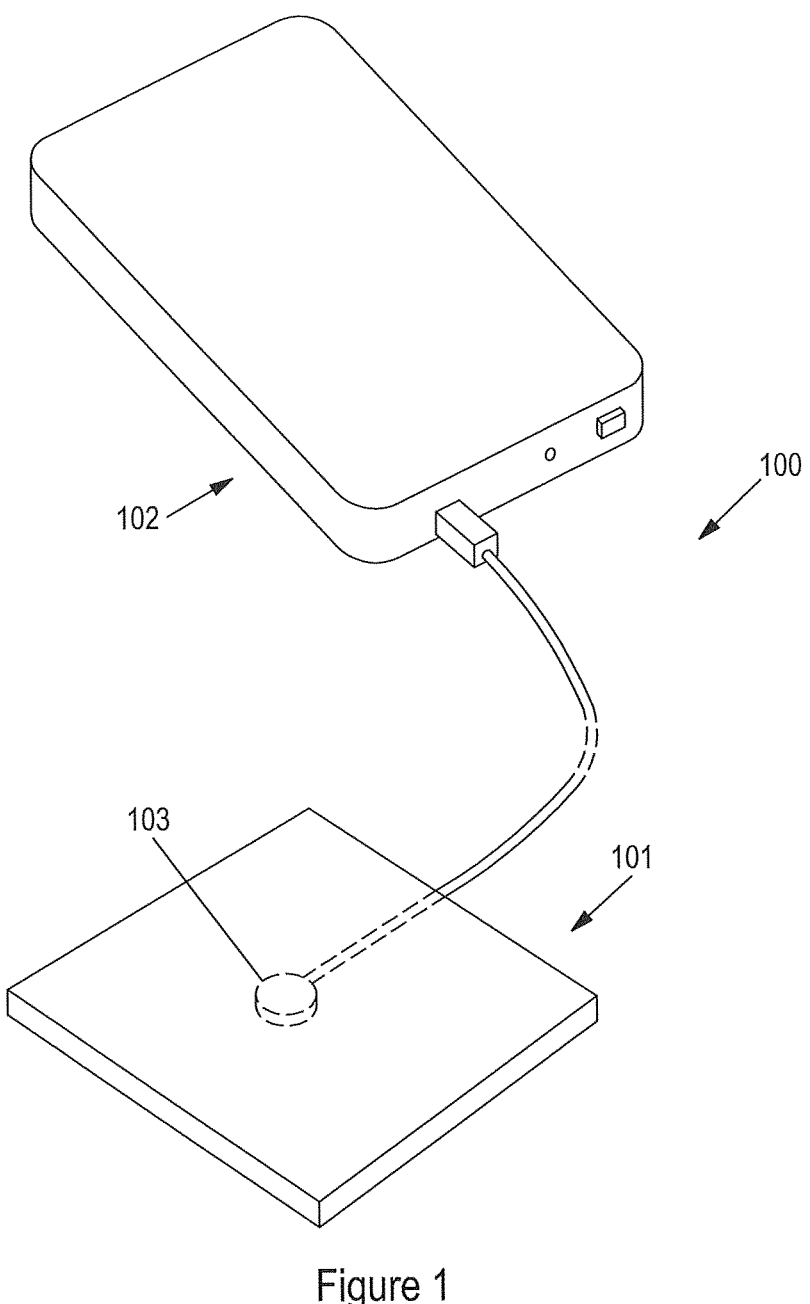
FIG. 1 herein illustrates schematically an electrostimulation treatment device comprising a drive unit and an electrostimulation patch according to a first specific embodiment FIG. 2a herein illustrates schematically in perspective exploded view a first electrostimulation treatment patch according to a second specific embodiment.

Referring to FIG. 1 herein, there is illustrated schematically in perspective view and apparatus 100 for treatment of a subject's body by electrostimulation. The apparatus comprises an electrostimulation patch 101, and a drive unit 102. The electrostimulation patch 101 is uniquely designed and manufactured for a particular body part of a particular individual subject, and receives a drive signal from the drive unit 102 which is created specifically for that particular electrostimulation patch, and for the individual body portion of the individual subject for which that electrostimulation patch is intended to be used with.

The electrostimulation patch 101 comprises one or a plurality of electromagnetic coils 103, individually selected for size, geometry and power output characteristics for the particular body portion of the subject for which the patch is intended to be used with, and the individual placement of the electromagnetic coil within a main body of the patch is made taking into account the size, geometry, type, and electromagnetic characteristics of the coil type. Preferably the coil is embedded in the patch 101, although it will be readily understood that the coil may be adhered to the side of the electrostimulation patch in contact with the patient's body.

The material of the electromagnetic patch 101 is resiliently deformable so as to allow the electromagnetic patch to be bent, twisted or deformed in order to fit the patch over the subject's body portion without applying undue stress or trauma to the body portion itself. The resilience of the material is selected such that once the patch is fitted to the subject's body portion, there is sufficient shape memory and sufficient stiffness of the material of the patch such that the patch can retain itself in situ without the need for any additional fixation such as glue, pins or straps, as the shape of the internal "U" shaped channel closely follows the external surface contours of the body portion to which the electro stimulation patch is fitted.

Figure 2A:
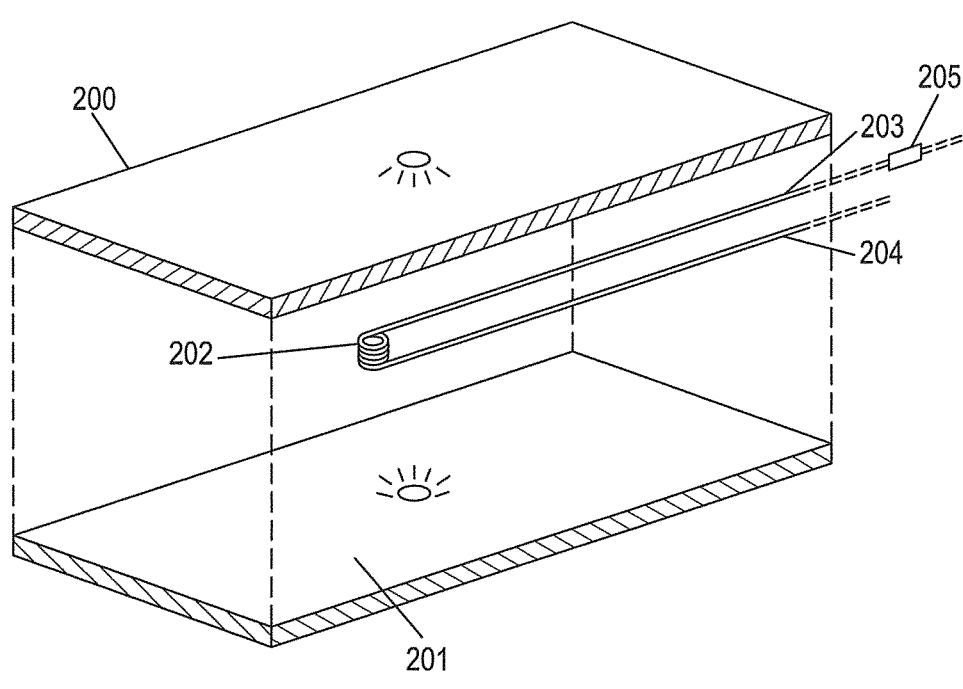
FIG. 2b herein illustrates schematically in perspective view, the first electrostimulation treatment patch of FIG. 2a herein.

Referring to FIG. 2a herein, there is illustrated schematically in exploded view an electromagnetic stimulation patch for promoting proliferation and/or generation of new organic cells via electromagnetic stimulation.

The patch comprises a first substrate material 200 in the form of a sheet material, said first substrate material having an upper surface, and a lower surface; a second substrate material 201 in the form of a second sheet said second substrate comprising an upper surface and a lower surface; at least one electromagnetic coil 202, said electromagnetic coil formed from an elongate strand or wire of conductive material for example copper wire, and having first and second leads 203, 204 which enable the electromagnetic coil to be connected to an external power supply, said strand or wire of conductive material having an external electrically insulating sheath material.

The electrostimulation patch is preferably provided with a unique identifier means 205 for uniquely identifying the patch. Said unique identifier means preferably comprises a memory chip and/or integrated circuit storing unique identifier data which uniquely identifies said electromagnetic stimulation patch. Preferably the unique identifier means is located at a distal end of the lead, 203, 204 away from the body or substrate of the patch, so as to be close to a drive unit used to supply a drive signal to the electromagnetic patch.

The electromagnetic stimulation patch is designed and manufactured on a bespoke basis, individualized to each patient, to be of a size and shape which closely fits an outer surface of the body region to be subjected to electromagnetic stimulation. The one or plurality of electromagnetic coils are positioned within the main body of the patch such that in use, the maximum electromagnetic field strength measured at a position on the outer surface of the electromagnetic patch is no more than 5 mT, preferably no more than 1.5 mT, and suitably less than 1 mT, so that if the outer surface of the electromagnetic patch is placed in contact with an outer surface of a body part to be subjected to electrostimulation, the maximum electromagnetic field strength at the outer surface of the body portion is 5 mT or less, preferably 1.5 mT or less, and suitably 1 mT or less, thereby avoiding genotoxic effect of electromagnetic radiation on body tissue.

As electromagnetic field strength decays with distance away from the electromagnetic radiation source according to an inverse square law, and as the target tissue region to be treated may be beyond the outer surface of the body part, the electromagnetic field strength produced by each electromagnetic coil at the target location of tissue to be treated, will be less than the electromagnetic field strength at the outer surface of the body part.

Figure 2B:
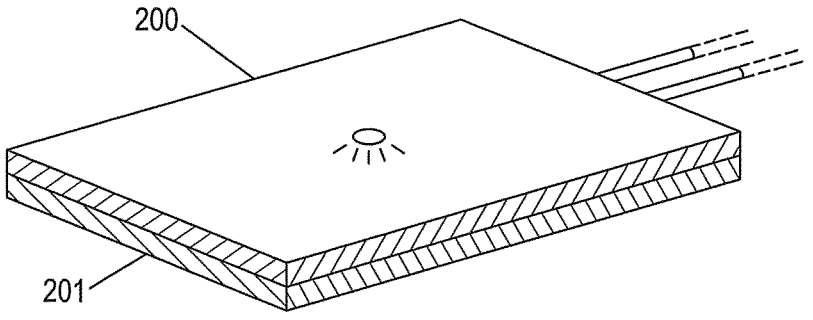

Referring to FIG. 2b herein, there is shown schematically in perspective view the electromagnetic stimulation patch FIG. 2a. The first substrate layer 200 is bonded to the second substrate layer 201, sandwiching therebetween the at least one coil 202. The conductive leads or tails 203, 204 of the coil 202 project outwardly between the first and second substrate layers for external connection to an electronic drive circuit.

In some embodiments, both the first and second substrate sheets formed of a pliable and/or deformable material having shape memory. The substrates may be mouldable around a body part so as to fit closely to a particular body part.

In other embodiments, the electromagnetic stimulation patch may be custom-made to a particular predetermined shape determined from measurements of a portion of a subject's body as will be described hereinafter. For example the stimulation patch may be fabricated as a formed mouth shield made to fit closely to a patient's jaw so that one or more said electromagnetic coils is placed immediately adjacent an area of the jaw which is to be subjected to electromagnetic field dosage treatment.

Other embodiments are not limited to a 2 layer construction, but in the general case may include an 'n'-layer construction, where 'n is a positive integer.

Coil Characteristics

In various embodiments intended for dental use, each electromagnetic coil has relatively small dimensions compared to prior art devices. The use of a smaller coil means that the coil(s) can be fitted between first and second substrate layers of a mouthpiece permitting a more comfortable fit for the user, rather than placing the coils on the surface of the mouthpiece as occurs in the prior art.

Since the field strength of an electromagnetic field diminishes in proportion to the square root of the distance away from the coil which generates said electromagnetic field, the ability to locate a relatively small coil closer to the treatment area petition to be treated means that a lower power can be applied to the coil to achieve the same required electromagnetic field strength at the treatment area, compared to prior art devices.

In the best mode embodiments, the coils used have the following characteristics:

Material: copper wire, anodised copper wire

Undeformed shape: circular; square; rectangular; elliptical.

Maximum field strength at 1 mm from plane of coil surface: 0.8 mT to 5.0 mT

However, in the general case, the number of windings or turns of wire in the coil may depend upon the wire thickness used, and the electromagnetic field strength which the coil is designed to produce. Wire thickness is in the range 0.001 mm to 3 mm may be used. Further, the number of turns or windings of individual coils may be in the range 10 to 10,000 turns, with the optimum number of turns or windings being in the range 30 to 500 windings, and preferably in the range 30 to 240 turns or windings or more preferably 60 to 180 windings.

Figure 3:
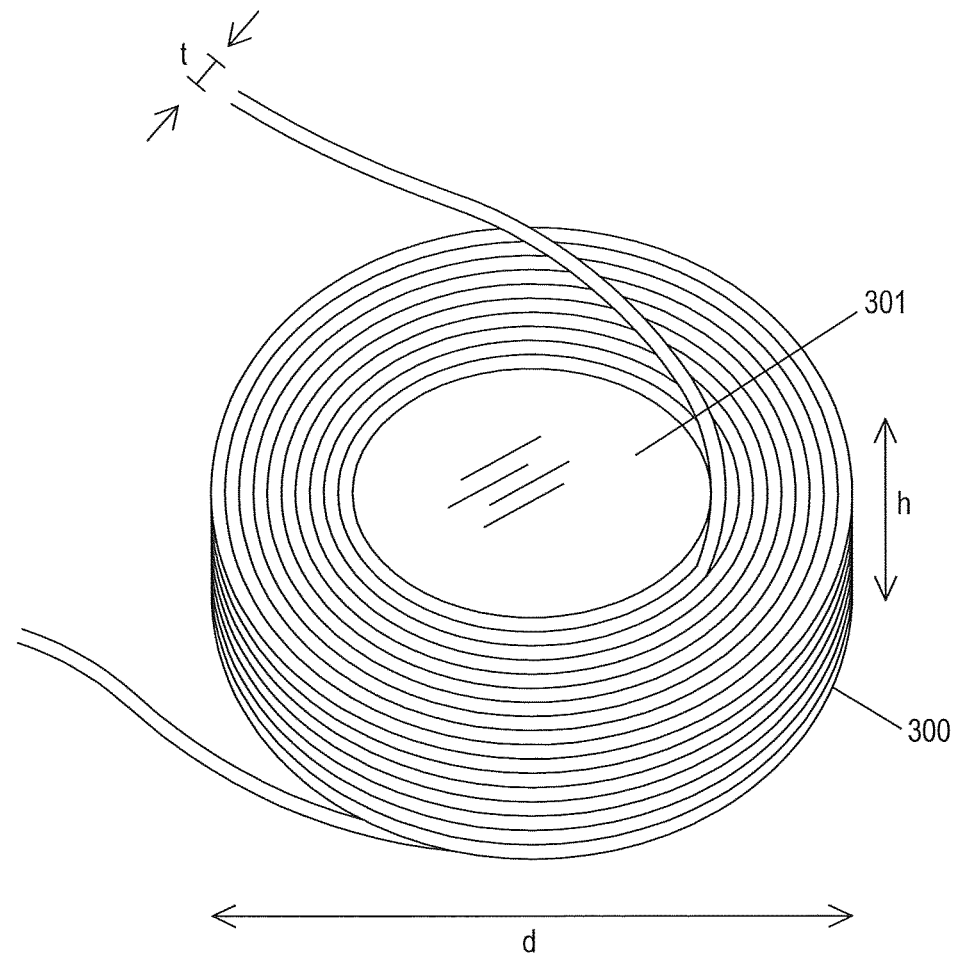
FIG. 3 herein illustrates schematically in front view, an electromagnetic coil having a ferrite core and a diameter, height and coil thickness denoted by d, h and t.

The electromagnetic coil 300 has a ferrite core 301. The length, width and height dimensions of the coil vary according to the number of turns of the coil and the electromagnetic power output which the coil is designed to achieve. Individual coils may have dimensions according to FIG. 3 in which in d=diameter of coil, h=height of coil and t=individual wire thickness in the following range:

Diameter: 0.01 mm to 15 mm

Height: 0.01 mm to 30 mm

Thickness: 0.001 mm to 3 mm

In the best mode, the coil dimensions may be as follows:

Diameter: 3.9 mm to 6.0 mm

Height: 3.5 mm to 4.5 mm

Preferred embodiments may have an individual wire thickness in the range 0.05 mm to 3 mm.

Preferred coil specifications may include the following:

Coil 1: 60 turns; outside diameter (width/length), 3.9 mm; height 3.64 mm

Coil 2: 120 turns; outside diameter (width/length), 5.6 mm; height 3.7 mm

Coil 3: 180 turns; outside diameter (width/length), 5.75 mm; height 4.8 mm

Whilst the coils may initially be manufactured in a substantially flat circular, square or other shape, in use due to the contours of the body part to which the coil is intended to fit next to, the coil may become deformed from a non-flat shape.

Preferably the above coils are capable of delivering electromagnetic field intensities in the range 1 to 5 mT either on a continuous basis, or on an intermittent basis.

Power Pack and Drive Electronics

Figure 4:
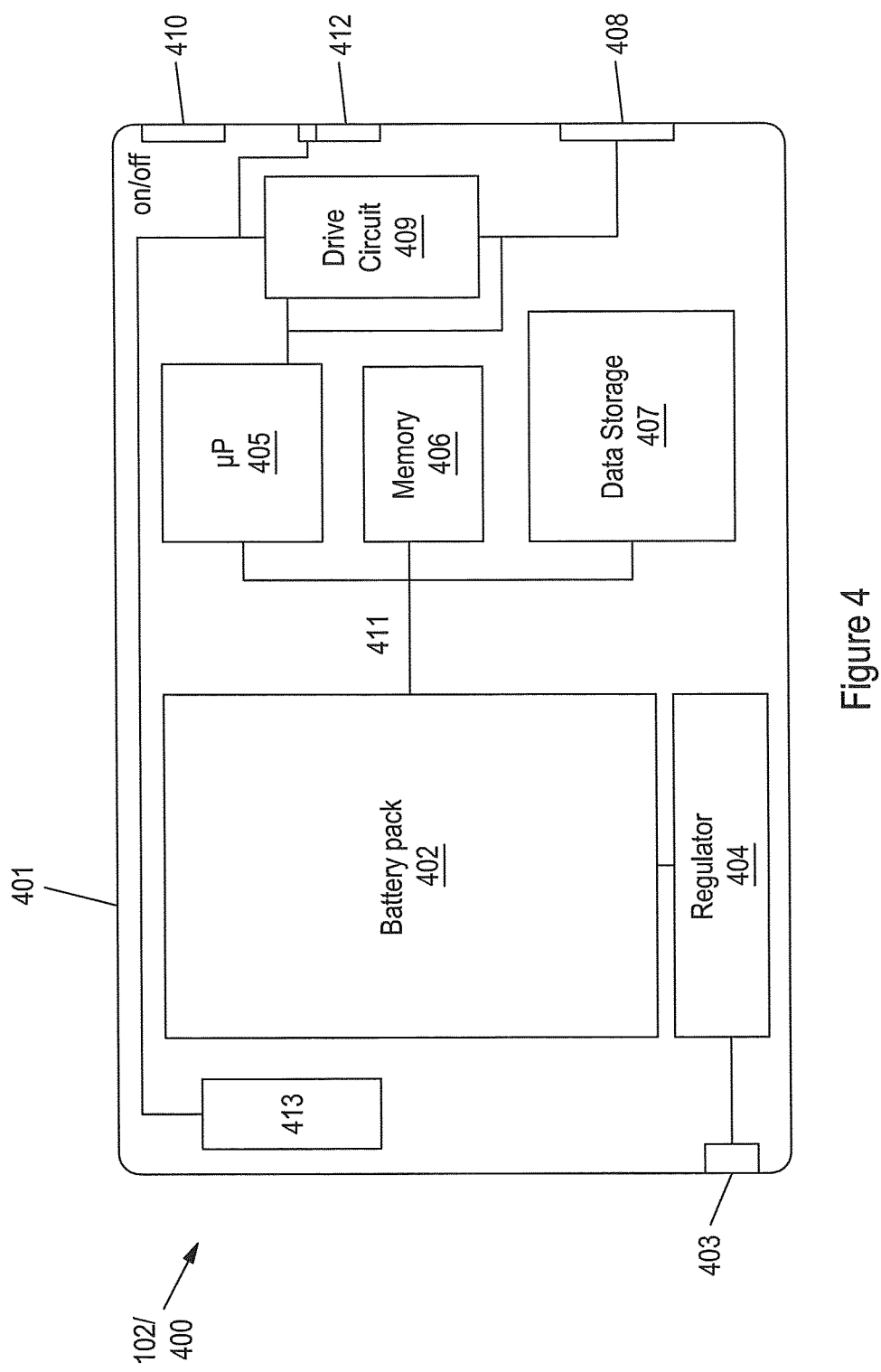
FIG. 4 herein illustrates components of the drive unit comprising the electrostimulation treatment device.

Referring to FIG. 4 herein there is illustrated schematically components of the drive unit 102/400 comprising a power pack and drive circuit used to energise an electrostimulation patch.

The drive unit 400 comprises a rigid outer casing 401 which contains all other components; a power supply, for example a rechargeable battery pack 402; a power connector port 403 for applying an external mains power supply or a DC power supply to the drive unit; a regulator circuit 404 for interfacing between the power connector port 403 and the battery pack 402; a microprocessor 405, for controlling the whole drive unit and applying a predetermined drive signal to an electrostimulation patch connected to the drive unit; a memory device 406, for example a random access memory (RAM); a data storage device 407, such as for example a solid-state hard drive for storing data describing drive signals for driving an electrostimulation device; a connector port 408 for connecting an electrical lead of an electrostimulation patch to the drive unit; a drive circuit 409 for applying a drive signal to an electrostimulation patch via the connector port 408; and on/off switch 410 for turning the unit on or off; an internal power and signal bus 411 for supplying power from the battery pack to the internal components and for signalling between said internal components; and one or more signalling devices such as an LED display, one or more lights or light-emitting diodes 412 for indicating an operating status of the drive unit.

In other embodiments, the power supply may comprise a capacitor for storing electrical charge.

The signalling indicator device 412 may give a visual indication of one or more states of the drive unit, for example a green light to show that the device is fully charged, an orange light to show that the device partially charged, and/or a red light to show that the drive unit battery is discharged. Alternatively battery charge status may be shown by virtue of a battery icon on an LED display. The display device 412 may also display a drive signal status, in a simple format showing whether the drive unit is delivering a drive signal to an electromagnetic coil or not, or in the case of multiple electromagnetic coils within the patch, a separate indicator for each electromagnetic coil indicating whether signal is being delivered to that coil or not.

Drive Unit Battery Charging

As the drive unit may be used by an untrained or unskilled subject user, in order to guard against risk of electric shock, the drive unit is configured such that it cannot be connected to an electromagnetic patch at the same time that the drive unit is connected to a power supply or to an a.c. mains supply for the purpose of battery charging. Preferably this safety feature is implemented such that an electrical connector on the drive unit for accepting an external d.c. battery charger, one end of which is plugged into an a.c. mains supply is used as both a battery charging port and as the socket outlet for an electromagnetic coil so that either an electromagnetic coil or a battery charger is plugged into the socket, but both cannot be physically plugged into the socket at the same time. A suitable socket may include a female micro USB socket as is known in the art, which provides both signalling capability, and power supply capability.

Figure 5A:
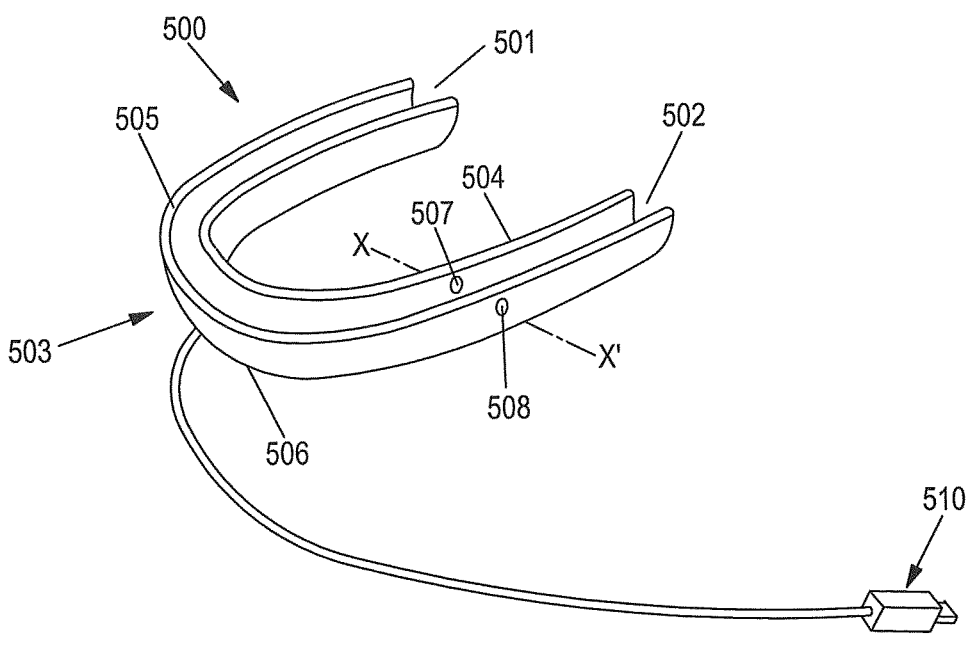
FIGS. 5a, 5b and 5c herein illustrates schematically a second electrostimulation device according to a second embodiment, in the form of a mouthpiece for dental electrostimulation.

Referring to FIG. 5*a* herein, there is illustrated schematically in perspective view an electrostimulation device 500 formed in the shape of a mouthpiece which extends around and over a patient's gums and upper or lower jaw. In the example shown, the mouthpiece is constructed to fit closely around a subject's upper jaw. The mouthpiece comprises a substantially "U" shaped piece comprising a first side portion 501; a second side portion 502; and a curved front portion 503. The first and second side portions and front portion form a substantially "U" shaped valley, having a first upright in a wall 504 and a second substantially upright outer wall 505, said inner and outer walls being joined together by a lower valley portion 506. The device 500 further comprises first and second electromagnetic coils 507, 508 positioned respectively on the inner and outer sidewalls and facing opposite each other across the substantially "U" shaped valley; and electrical connector lead 509 preferably attached to the front incisal edge of the device which supplies a drive signal to each of the electrostimulation coils 507, 508; said electrical connector lead 509 having a termination connector 510, which may be in the form of a conventional plug and socket communications connector, for example a USB or micro-USB male or female connector for connecting the first and second electrostimulation coils 507, 508 to a drive unit for applying an electrical signal to the coils.

The electrical connector lead 509 comprises a plurality of individual conductor wires, in order to power the individual electromagnetic coils embedded in the body of the mouthpiece. In the embodiment shown, there are two individual electromagnetic coils, each having two conductor wires, making four individual conductor wires in the electrical connector lead 509. This enables the first and second electromagnetic coils 507, 508 to be individually driven by a separate drive signal so as to enable that the first coil 507 can be independently driven with a different signal pattern and/or signal power to the horizontally opposed second electromagnetic coil 508.

The electro-stimulation device 500 further comprises an identification device which may be located in the moulding around the connector plug 510, which may uniquely identify the electrostimulation device to a drive unit. The unique identification may be carried out by various devices including a radio frequency identification tag (RFID), or by a microchip within the housing of the connector 510 which has a unique digital code and which may be interrogated by the drive unit via the connector 510. The unique code may comprise a MAC address, so that the electrostimulation device 500 uniquely identifiable over the Internet by its unique Internet address.

It will be appreciated that whilst in FIG. 5*a*, an embodiment of the bespoke mouthpiece/mouthguard is shown, having first and second horizontally opposed electrostimulation coils, in other embodiments either one, two, three or more individual electrostimulation coils may be provided in order to apply electrostimulation treatment at more than one treatment site, for example at the root of more than one individual tooth. Each electromagnetic coil may be individually driven with a different drive signal specific to that electromagnetic coil.

Figure 5B:
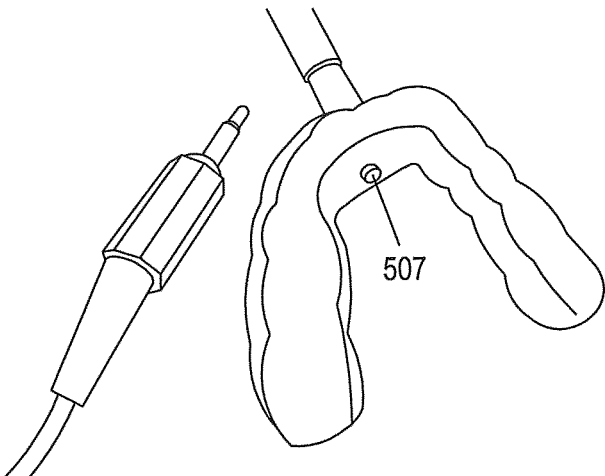
Figure 5C:
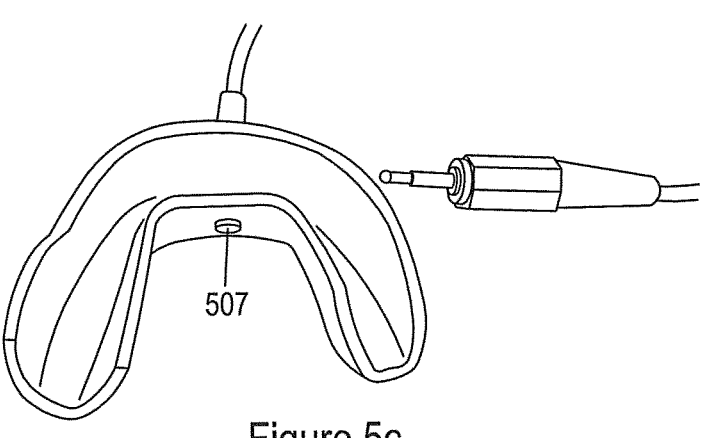

FIGS. 5*b* and 5*c* herein illustrate the best mode embodiment of the invention a custom-made, user specific mouthguard modified to incorporate at least one electromagnetic coil 507 to stimulate a user's cells with electromagnetic signal.

Figure 6:
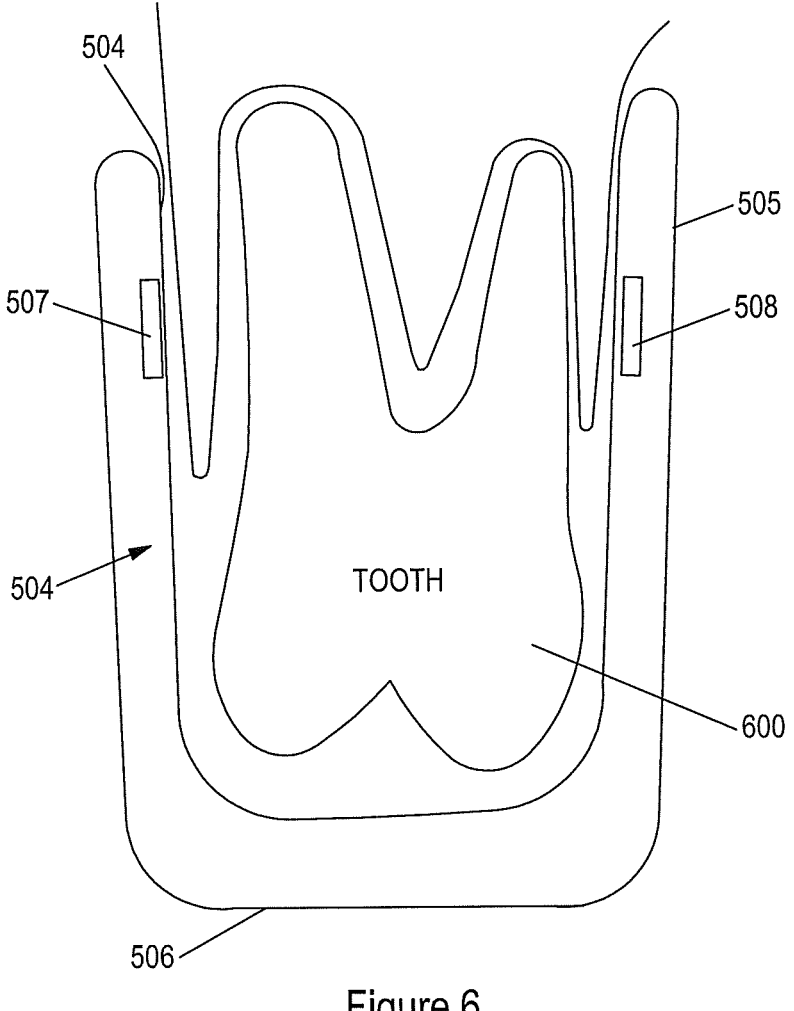
FIG. 6 herein illustrates schematically in cutaway view a section of the second electrostimulation treatment patch of FIG. 5a herein, in situ around a tooth.

Referring to FIG. 6 herein, there is illustrated schematically in cut away view across the section X-X' shown in FIG. 5*a*, the arrangement of first and second horizontally opposed coils 507, 508 either side of a tooth portion 600 when the mouthpiece of the electrostimulation device 500 is fitted in situ in a subject's mouth.

The mouthpiece wall is constructed of a first inner layer 504 of mouldable settable material laminated to a second, outer layer 505 of mouldable settable material. Shown in FIG. 6 is a cross-sectional view of the substantially "U" shaped mouthpiece after it has been formed around the upper jaw portion of the subject, such that the inner and outer walls 504, 505 and the base portion 506 closely fit the external surface of the body part, in this case an upper jaw and row of teeth, of the subject.

The wall material of the mouthpiece is individually formed so that the inner surface of the mouthpiece may closely follow and/or may contact the outer surface of the body portion which it is intended to lie adjacent to. This enables the individual electromagnetic coils 507, 508 to be placed accurately, within a distance of a few millimetres, typically a distance 0.1 mm to 1.0 mm from the outer surface of the body portion. Further, each individual electromagnetic coil can be positioned accurately in the horizontal, vertical and lateral directions X, Y and Z respectively, with a relatively high degree of accuracy, the range 0.1 mm to 1.0 mm, with respect to a target tissue region of the subject which is to be subjected to electromagnetic radiation.

In the example shown in FIGS. 5*a* and 6, in use, a drive signal is applied to each of the first and second electromagnetic coils respectively according to a predetermined programme of electric drive signal which specifies parameters comprising the following:

average voltage and/or current;
average power;
period p of drive signal;
pulse duty cycle of drive signal;
pulse width;
pulse shape;
A. C or D. C drive signal.

Figure 7:
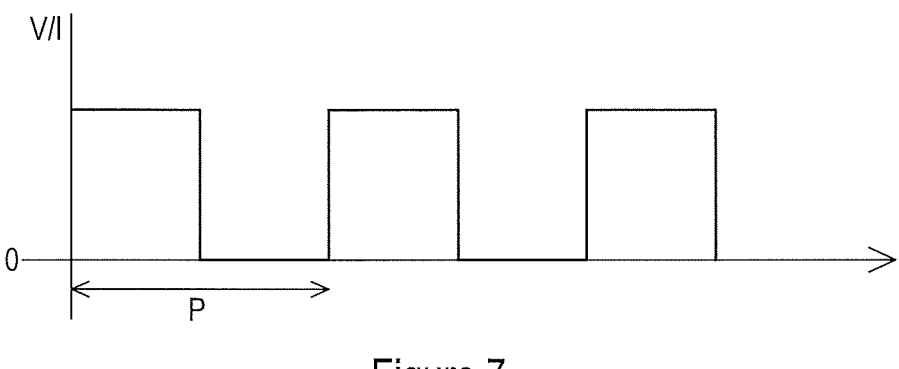
FIG. 7 herein illustrates schematically a first example DC drive signal produced by the drive unit.
Figure 8:
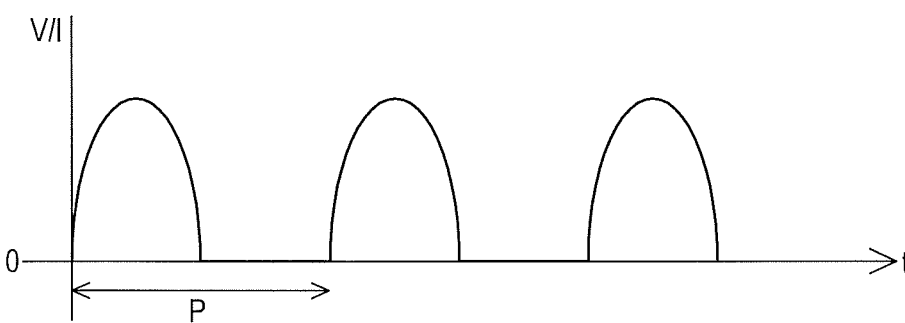
FIG. 8 herein illustrates schematically a second example DC drive signal produced by the drive unit.
Figure 9:
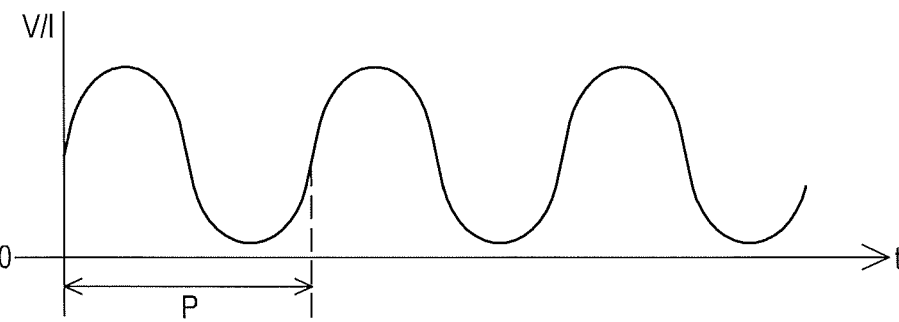
FIG. 9 herein illustrates schematically a third example DC drive signal produced by the drive unit.

Referring to FIGS. 7 to 9 herein, there is illustrated schematically 3 individual examples of drive signals to the electromagnetic coils which may be applied. Each drive signal comprises a drive current having a digitally synthesised waveform envelope comprising a plurality of individual digital current pulses.

In FIG. 7 herein, there is illustrated a basic direct current square pulse having a 50% duty cycle, with period P and voltage or current V, I respectively.

In FIG. 8 herein, there is illustrated schematically a direct current half sine wave having a 50% duty cycle, with period P, and maximum voltage V or maximum peak current I.

Referring to FIG. 9 herein, there is illustrated schematically a full direct current sine wave having period P and maximum voltage V, and maximum current I.

The above drive signals are examples only, in principle any drive signal waveform may be applied including triangular, saw tooth, or specific waveforms. A specific waveform is generated using software by plotting a number of points of that waveform. The number of points is of the order of tens of thousands of points per second. The frequency, amplitude and all other characteristics of the waveform are optimised to provide a patient specific waveform. The voltage and current are the two elements which together provide the power characteristics according to the calculation P=IV. Whilst the overall waveform envelope is shown, the waveform envelope itself may be digitally synthesised from a series of individual digital pulses.

The voltage and current are specific to the type of treatment being applied to the individual specific patient. Current may then be from 5 mA to 10 A and voltage from 5 mV to 500V. Typically the device is operated between 0.5V and 12V, preferably at 3V and in a range from 50 to 1000 mA although specific treatments may require these parameters to be varied outside this range. Frequency may be from 0.5 Hz to 500 Hz with the typical frequency being in the range 5 Hz to 8 Hz. The delivery of EMF waveform may be applied continuously or intermittently, according to the specific patient and specific treatment.

All these parameters are determined by software which uses data provided by the dental surgeon which specifies the location of the target site in the patient's mouth, combined with data from the process of producing the bespoke mouthguard which determines the distance of the coil from the target site, the coil location material, the orientation of the coil, the output of the coil (which is itself a function of the coil dimensions).

Parameters for the drive signal envelope are in the range as follows:

voltage: 5 mV to 500V current: 5 mA to 10 A

Frequency F of drive signal: 0.5 Hz to 500 Hz

Typically the device is operated at 3V and in a range from 50 to 1000 mA with a frequency in the range 5 Hz to 8 Hz.

Figure 10:
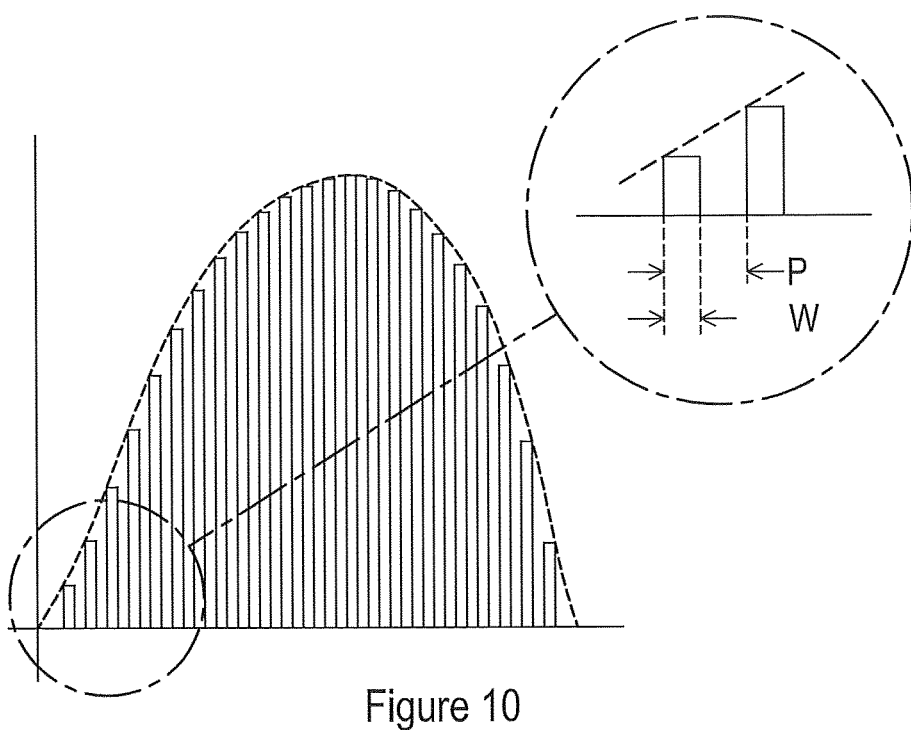
FIG. 10 herein illustrates schematically in greater detail, a portion of the second example drive signal of FIG. 8 herein.

Referring to FIG. 10 herein, there is illustrated part of a direct current half-sinusoidal waveform as shown in FIG. 8 herein showing how the half sinusoid wave form envelope is digitally synthesised from a plurality of higher frequency digital pulses. Within the overall half-sinusoidal envelope, are a plurality of individual DC pulses, whereby the maximum amplitude of each individual DC pulse forms the overall envelope shape of the digitally synthesised waveform. The individual relatively higher frequency digital pulses themselves may have variations of higher frequency period p, higher frequency pulse width w, and higher frequency duty cycle so that the amount of power going into the envelope waveform can be varied by varying higher frequency pulse of period p, higher frequency pulse duty cycle, and higher frequency pulse width w.

Typically, each cycle of the overall waveform envelope contains between 1,000 and 10,000 individual digital pulses.

Figure 11:
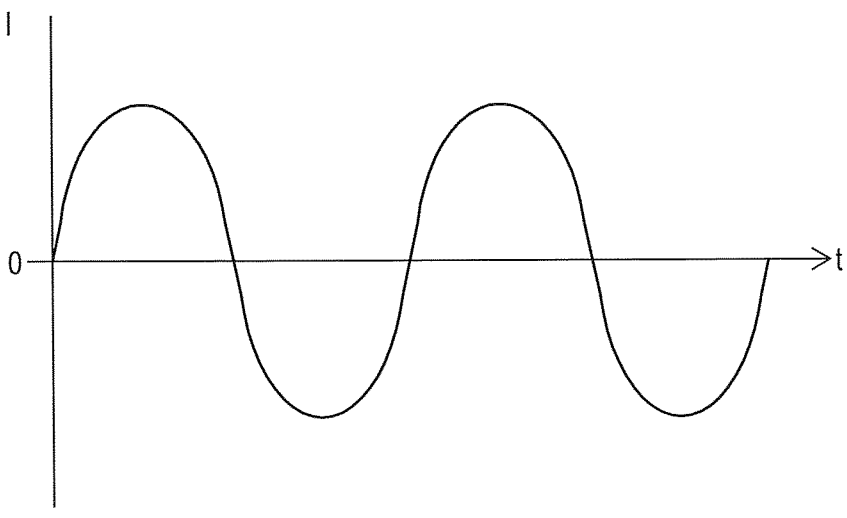
FIG. 11 herein illustrates schematically a waveform envelope of an AC sinusoid drive signal produced by the drive unit.

Referring to FIG. 11 herein, there is illustrated schematically a further drive signal having an overall envelope in the form of a sine wave. The drive signal shown in FIG. 11 is constructed from a large number of individual digital pulses, between 1,000 and 10,000 individual pulses for each cycle of the main sine wave envelope. The signal in FIG. 11 is an alternating current signal, whereas the signals in FIGS. 7 to 9 herein are each direct current drive signals.

Manufacture, Provision and Operation of Electromagnetic Patch

In the specific embodiments and methods described herein, each treatment patch may be manufactured on a customised per device basis so that its dimensions and layout are optimised to provide a predetermined electromagnetic field strength in the three-dimensional region occupied by the tissue to be treated for a specific subject or patient and specific body region of that subject. Each patch is designed and customised to treat a particular tissue region of a particular body part of a particular specific subject user.

Figure 12:
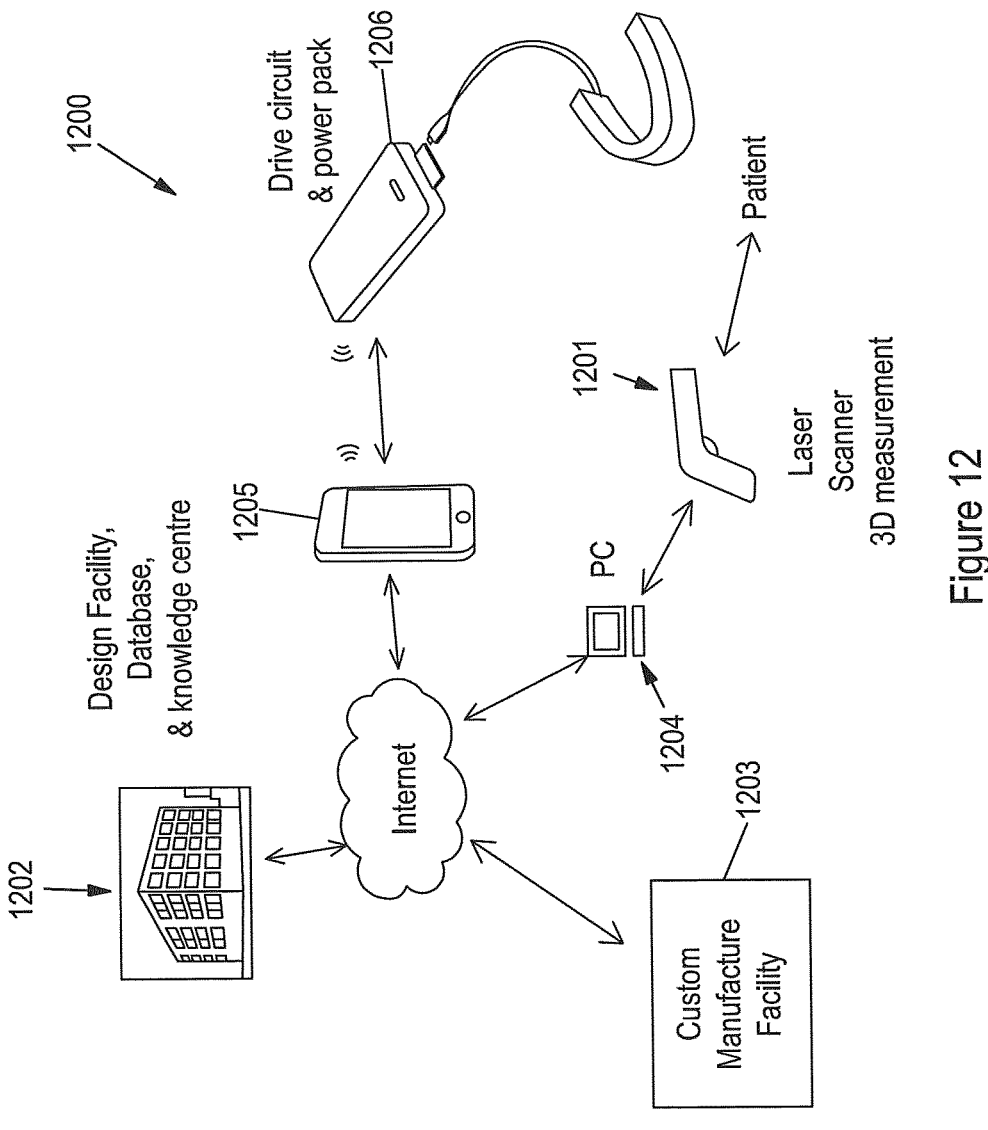
FIG. 12 herein illustrates schematically a system and apparatus for bespoke manufacture and personalised treatment of a plurality of patients using electrostimulation treatment devices.

Referring to FIG. 12 herein, there is illustrated schematically components of an overall comprehensive fulfilment system and apparatus for providing electromagnetic treatment devices which are customised to individual subjects and to individual regions of tissue to be treated, together with bespoke electromagnetic treatment programmes tailored to the individual subject and tissue region to be treated.

The fulfilment system and apparatus 1200 comprises one or more data inputs and/or data input devices 1201 which may for example comprise a laser scanner, an image of a 3 dimensional dental impression of a patient's dentition, or manually entered numeric data e.g. molar number 32, upper jaw; a design facility 1202 for designing treatment devices and creating electromagnetic treatment programmes for individual subjects; a manufacturing facility 1203 for manufacturing treatment devices; and one or a plurality of communications devices 1205 for communicating between the drive unit 1206, data input devices 1201, design facility and knowledge centre 1202, and custom manufacturing facility 1203.

In the general case, individual components of the fulfilment system and apparatus may be distributed geographically away from each other and may communicate with each other over the internet or a virtual private network (VPN), or other communications network. However, in other specific implementations various components of the fulfilment system may be more conveniently co-located with each other in a single building or in separate buildings on a same site, for example in a hospital or other medical facility.

Figure 13:
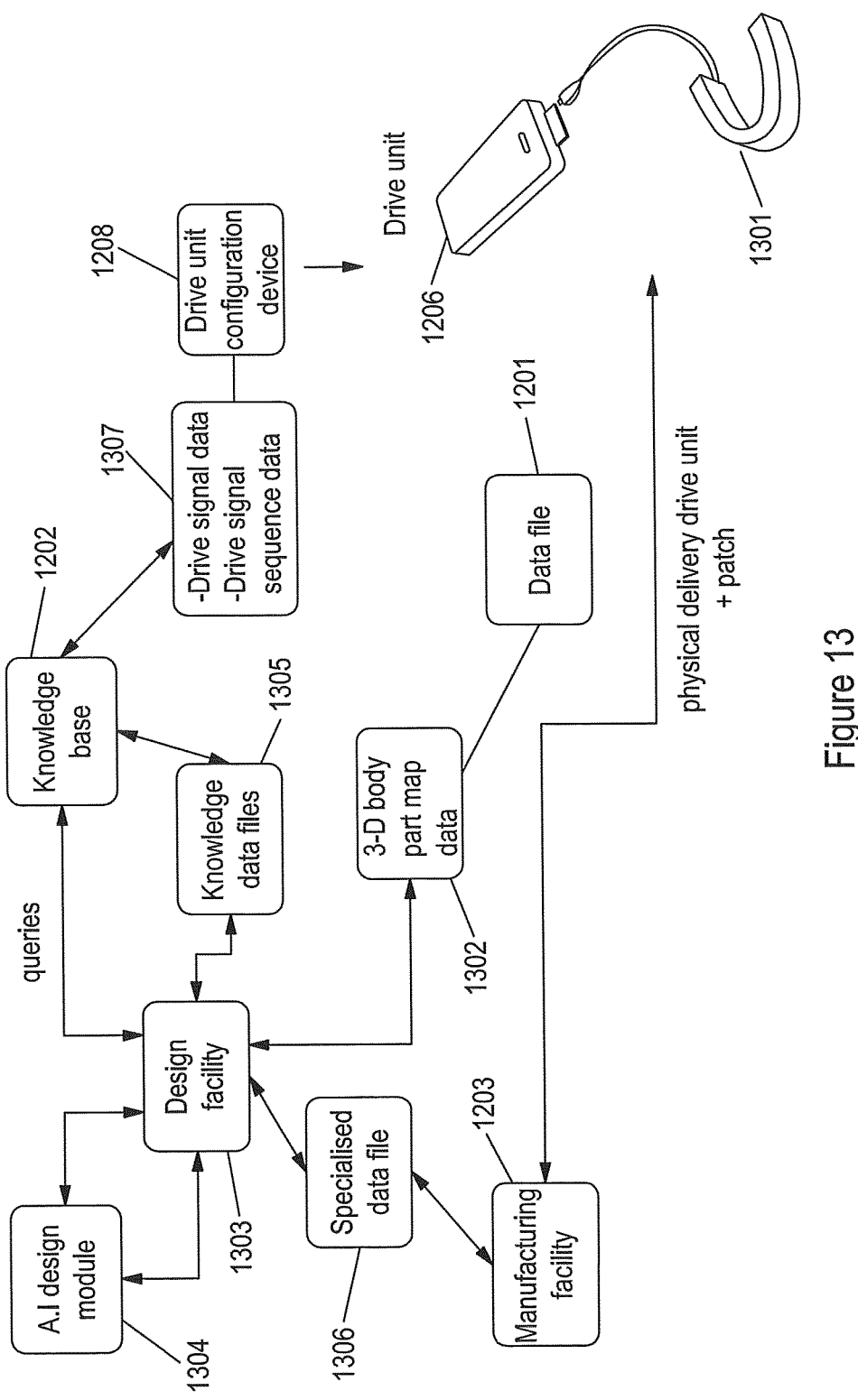
FIG. 13 herein illustrates schematically an overall process for delivering a customised subject-specific electromagnetic stimulation treatment programme using the system and apparatus of FIG. 12 herein.

Referring to FIG. 13 herein, there is illustrated schematically operation of the fulfilment system and apparatus of FIG. 12 herein to produce a drive unit 1206 and electromagnetic stimulation device 1301 suitable for an individual subject user. The processes described with reference to FIG. 12 are not restricted to being done in the sequence presented herein below and each individual process may be done independently and in parallel with other processes, or iteratively with other processes subject to the constraints of each individual process having timely access to the necessary input data available from other said processes.

A data file 1201, which may be electronic data obtained from a scan of a physical dentition impression or data manually input into a database by a physician to identify the injury site e.g. lower jaw molar number 32, is used by, preferably a trained medical practitioner or technician, to create a three-dimensional map data 1302 of a body region containing an area of cells which are to be treated using electromagnetic field regeneration. The three-dimensional map data comprises a plurality of individual data points, each describing an individual point in three-dimensional reference space, wherein an internal and/or external surface feature of a body part surface is defined by a set of said individual data points. For example, the surface of the body part may comprise the outer surface of one or more teeth, and an outer surface of a gum portion adjacent said one or more teeth. In another example, the three-dimensional map data may describe the complete upper palate, and upper jaw of a subject. In a further example, the three-dimensional map data of a body part may comprise a plurality of individual data points describing the surface of a lower jaw and lower tooth set of an individual subject. Whilst the present examples refer to a subject's mouth, the processes are not restricted to any particular anatomical feature and in the general case can be applied to any anatomical feature of the subject.

The three-dimensional map data 1302 generated by the data file is sent to the design facility 1303 as an electronic knowledge data file, for example either over the Internet, or saved on a data storage media and physically transferred.

The design facility preferably comprises the manual placement of an electromagnetic coil according to the electromagnetic frequency measured using a Gauss meter as per the apparatus of FIGS. 38 and 39. Alternatively, the design facility may comprise a computer aided design suite which may be based upon a known computer aided design package, for example Solid Works®, Autocad® of Dassault Systems or the like as the base functionality platform, and may be augmented with an artificial intelligence design module 1304. The design suite 1303 may alternatively be provided as a login service accessible remotely over the Internet.

The design facility utilises the knowledge data files 1305 to create a three dimensional map 1302 from the data files 1201, and saves the data in a knowledge base 1202, which can then be modified and manipulated by a human designer at the design facility 1303.

Details of individual coil types are stored in knowledge base 1203. The coil data file contains information describing one or more individual coil types, including: wire type; wire material; wire thickness; wire length; overall coil shape; number of turns of coil; maximum current, voltage or power rating of coil. Details of the ferrite insert are also stored here including: length; depth; or diameter; height; or other irregular dimensions; material specifications and performance characteristics.

The knowledge base 1202 also contains data describing a plurality of predetermined drive signals for driving each individual coil type. This drive signal data may also be included in the coil data file retrieved from the knowledge base 1202.

The design facility 1303 creates a three-dimensional electromagnetic field model comprising a plurality of points in three-dimensional space, with an electromagnetic vector field strength at each point. The electromagnetic field model data may be compared with the three-dimensional body portion map data and a three-dimensional data describing a target tissue region of said body portion.

The design facility may then manipulate the design module using a pointing device, monitor and keyboard, to obtain an arrangement of coil position, including coil location at coil orientation with respect to the body portion and the tissue region to be treated, at which a selected coil produces a required electromagnetic field strength when driven by a selected drive signal.

Since there may be more than one combination of coil type, drive signal and many variations of position which all give acceptable electromagnetic field strengths throughout the target tissue region, and which all give electromagnetic field strength throughout the remainder of the body portion which are lower than genotoxic levels, optimisation is carried out to narrow down the number of possible coil positions, coil types, and drive signals for the particular specific body portion subject of the three-dimensional body map data and the particular tissue region which is to be treated.

The optimisation can be performed with human intervention, for example by selecting from experience different coil types, drive signals and through knowledge and skill of the human operator, positioning the coil in an optimum position, or at least a position where result is obtained.

Alternatively, and/or in addition to human selection of coil position, coil type, and drive signal parameters, the artificial intelligence module 1204 may be used to select any or all of these variables to arrive at a viable coil type, coil position and drive signal parameter which will satisfy the required electromagnetic field strength and dosage criteria for treatment of the tissue, and to satisfy the maximum levels of electromagnetic field strength experienced by other adjacent body parts to avoid genotoxic effect.

Once an acceptable set of parameters for coil type, coil position, drive signal parameters and three-dimensional shape of the electromagnetic patch to fit the specific body portion and tissue region under consideration, a specification data file 1306 is generated from which an electromagnetic patch having the required coil type, coil position and three-dimensional shape of patch can be manufactured. The patch specification data file is sent to manufacturing facility 1203 for manufacture.

The patch specification data file comprises the following types of data:

data specifying the external shape of the electromagnetic patch;

data describing the number, type and positions of individual coil is to be incorporated into the substrate of the electromagnetic patch;

individual identification data to identify an individual patch once manufactured;

data describing the type of identification means to be used, for example a unique identifier data which uniquely identifies said electromagnetic stimulation patch;

data describing the material type for manufacture of the substrate or body of the electromagnetic patch.

On receiving the specification data file 1307 from the design facility 1303, the manufacturing facility 1203 proceeds to manufacture one or more electromagnetic patches corresponding to the specification. If more than one electromagnetic patch having the same specification is created, each individual electromagnetic patch may still be given a unique identification number or code so that no two individual electromagnetic patches can be confused. Alternatively, where there are identical electromagnetic patches having identical specification, an individual identification code may be given to the patch type having that particular specification, since each patch of identical specification is substitutable for another. In the best mode, each individual patch is given its own individual unique identification code or number.

The design facility also generates drive signal data 1208 used for driving individual electromagnetic coils within an electromagnetic patch. The drive signal data is specific to an individual electromagnetic patch specification (which may include more than one electromagnetic patch if a plurality of electromagnetic patches are manufactured for an individual subject, all identical and the same specification).

The drive signal data is specific to the individual electromagnetic patch specification which has been created for an individual tissue region of an individual subject user. The subject tissue region specific drive signal data specifies the individual drive signals to be sent to each electromagnetic coil in a particular specific electromagnetic patch designed for treating that tissue region of that particular subject user.

Thus, whilst the electromagnetic patch itself is configured for a specific tissue region of a specific subject user, the drive signal data for that specific electromagnetic patch is also specific to that specific region of that specific subject user. However, within the drive signal data, there may be contained one or more different drive signals for each of the individual coils within the electromagnetic patch, and different drive signal sequences, being one or more drive signal sequences, each individual electromagnetic coil within a specific electromagnetic patch.

The drive signal sequence represents a series of drive signals applied to a particular coil. For example the drive signal itself may be a ½ drive signal envelope applied at a particular current to a particular coil. The drive signal sequence may specify for how long the drive signal is applied (duration of signal application) periods during the day when the signal is not applied, periods during the day when the signal is applied. In this way, a dosage programme can be controlled by the drive units applying a particular signal type over a particular duration, with intervals between applications of the signal where the on/off times of the signal are determined by the drive signal sequence. The drive signal sequence can therefore effectively apply a pre-programmed dosage of electromagnetic field to a tissue region of a specific subject user, using an electromagnetic patch which is designed for that specific tissue region of that specific subject user.

The drive signal data and drive signal sequence may be sent from the design centre 1202 to the manufacturing facility 1204, which may also manufacture drive units, so that at the manufacturing facility, a particular drive unit can be programmed by downloading the drive signal data and drive signal sequence data file 1307 at the point of manufacture.

Alternatively, where a drive unit has already been manufactured and shipped to the subject user, the drive signal data and drive signal sequence data 1307 may be downloaded over the Internet from the design suite to a drive unit configuration device 1208 which can be used to program the drive unit 1206.

In order to prevent the drive signals and drive sequence specific to a particular electromagnetic patch being used with a different electromagnetic patch, the drive signal data file also includes a unique code or number which identifies the individual electromagnetic stimulation device or patch 1301 specified for a particular subject user. On connecting the electromagnetic stimulation device/patch 1301 to the drive unit, if the identification code or number of the data file for the drive signals and drive sequence does not match the identification code number for the electromagnetic patch, then the drive circuit of the drive unit is inhibited from supplying power to the electromagnetic patch.

The drive unit may recognise an individual electromagnetic patch or patch type by means of a recognition means. The recognition means may comprise an integrated circuit storing a unique identifier data which uniquely identifies said electromagnetic stimulation patch.

Figure 14:
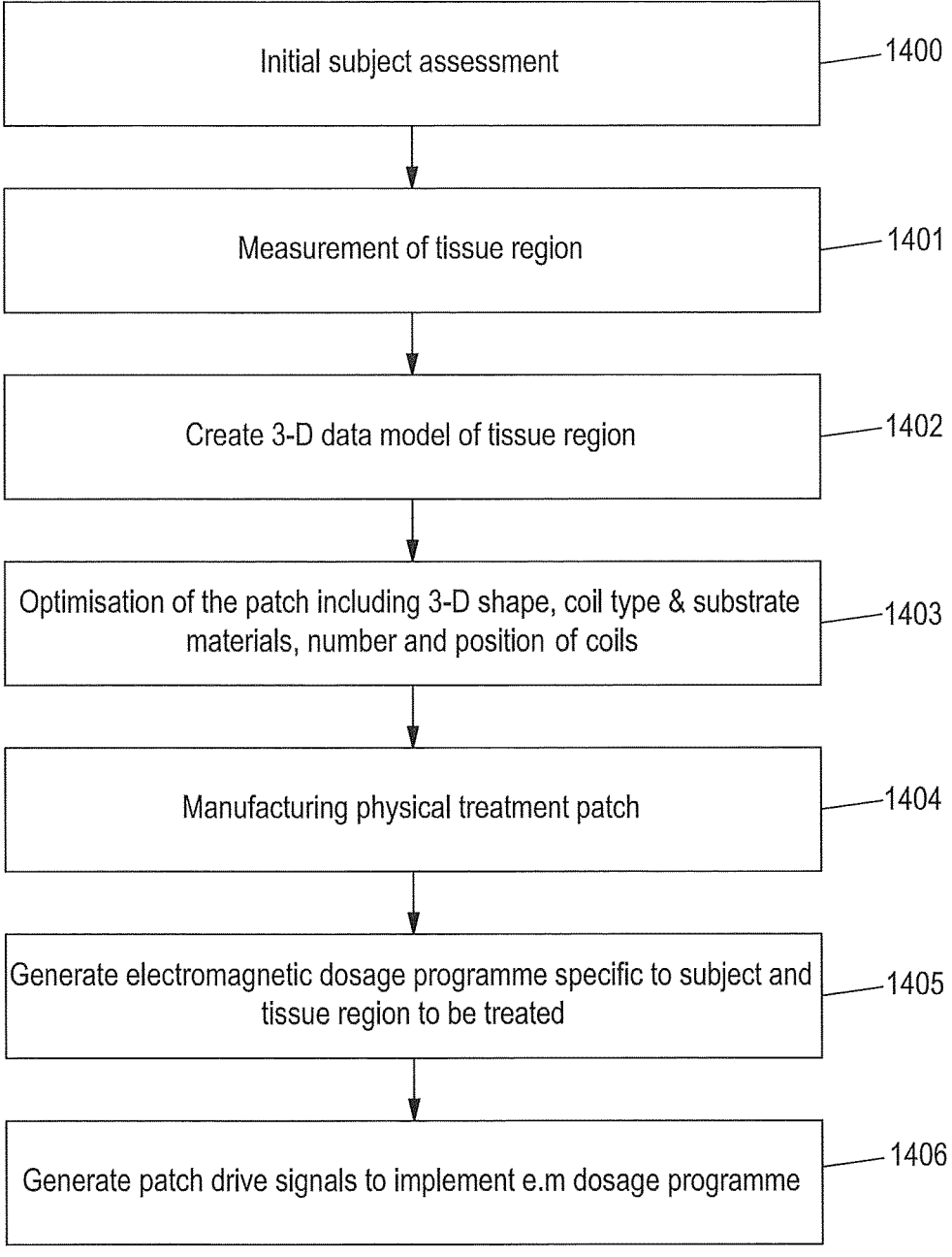
FIG. 14 herein illustrates schematically procedures for an overall process for delivering a customised subject specific electromagnetic stimulation treatment programme to a subject.

Referring to FIG. 14 herein, production of a bespoke customized treatment device and a dosage treatment programme corresponding to the treatment device comprises the following operations:

Initial assessment of the subject 1400;

Measurement 1401 of the target tissue region to produce a 3-dimensional data model of the tissue region to be treated;

Creating a 3-dimensional data model 1402 for a treatment patch.

Optimising the shape of patch, substrate materials, number of electromagnetic coils, positioning of electromagnetic coils(s) on the patch, for the particular subject and particular tissue region;

Manufacture of a treatment patch 1404, according to the design specification of the computer generated design;

Generating an optimised programme of electromagnetic radiation 1405 specific to a subject and tissue region to be treated; and Generation 1406 of a set of patch signal data for providing drive signals to the patch, in order to produce the optimised programme of electromagnetic radiation specific to the subject and tissue to be treated.

In the initial assessment process 1400, a human operative first assesses the subject for suitability of treatment using the electromagnetic stimulation method. This assessment includes a general assessment of health or fitness, and suitability for treatment using electromagnetic radiation, as well as an assessment of the subject's specific tissue region to be treated.

The human operative may be a qualified health professional such as a doctor, nurse, dental surgeon, physician or other health specialist. The human operative has access to the online data stored in the centralised data and knowledge base, and can refer to any written procedures stored in the knowledge base, or can query the knowledge base to check and consult on the specific details and intricacies of any assessment, measurement or other procedure stored in the knowledge base.

In the measurement process 1401, there is created a 3-dimensional data which represents the outer surface of the tissue region to be treated and optionally internal structures of the tissue region to be treated. The measurement process may comprise one or more of the following:

using a known 3-dimensional laser scanner to record a plurality of datum points on the skin of a subject, to create a 3-dimensional map of a section of a person's body;

Making a cast or mould of a body part using a known settable material or a deformable material such as plaster of Paris (impression plaster, impression compound, zinc oxide eugenol paste (impression paste), and impression wax's such as hydrocolloid, agar, alginate, a non-aqueous elastomeric impression material such as a poly sulphide; a polyether, or silicones, followed by making 3-dimensional measurements of the cast or mould as a proxy for the body part;

making 3 dimensional measurements directly on the surface of the body part, using a reference frame and measuring instruments such as a ruler, calipers, and a protractor.

A specification of the patch is created in process 1403 using the 3-dimensional map data of the body portion to be treated in conjunction with specification data representing characteristics of individual coil types, comprising coil width, height, depth, shape, wire thickness, wire material, body material, maximum power output; ferrite length, depth, or diameter, height or other irregular dimensions, material specification and performance characteristics; electrical characteristics such as resistance; and substrate material specification data comprising material thickness, material pliability, material strength, electromagnetic transmission properties of the material, bonding properties of the material and/or any adhesive used to add here the substrate to another substrate; number of coils required; and a position or location data in 3 dimensional coordinates of a specific tissue region to be treated within the larger set of 3-dimensional body portion data.

The specification of the patch is effectively a design for the patch as it specifies all parameters needed in order to manufacture patch.

In process 1404, the physical patch is manufactured. The patch can be manufactured using a variety of techniques ranging from custom-made fabrication by a skilled artisan or craftsperson through to 3-dimensional printing of the first and second substrates around one or more coil components.

In process 1405 there is generated an electromagnetic dosage programme which is specific to an individual subject and tissue region of said subject to be treated.

In process 1406, the manufactured patch is applied to the subject for which it has been specifically created and a drive signals are applied to patch in order to provide the appropriate electromagnetic signal levels from the coils to give the desired signal power in the region of tissue to be treated, and according to the specific dosage programme which has been generated.

Figure 15:
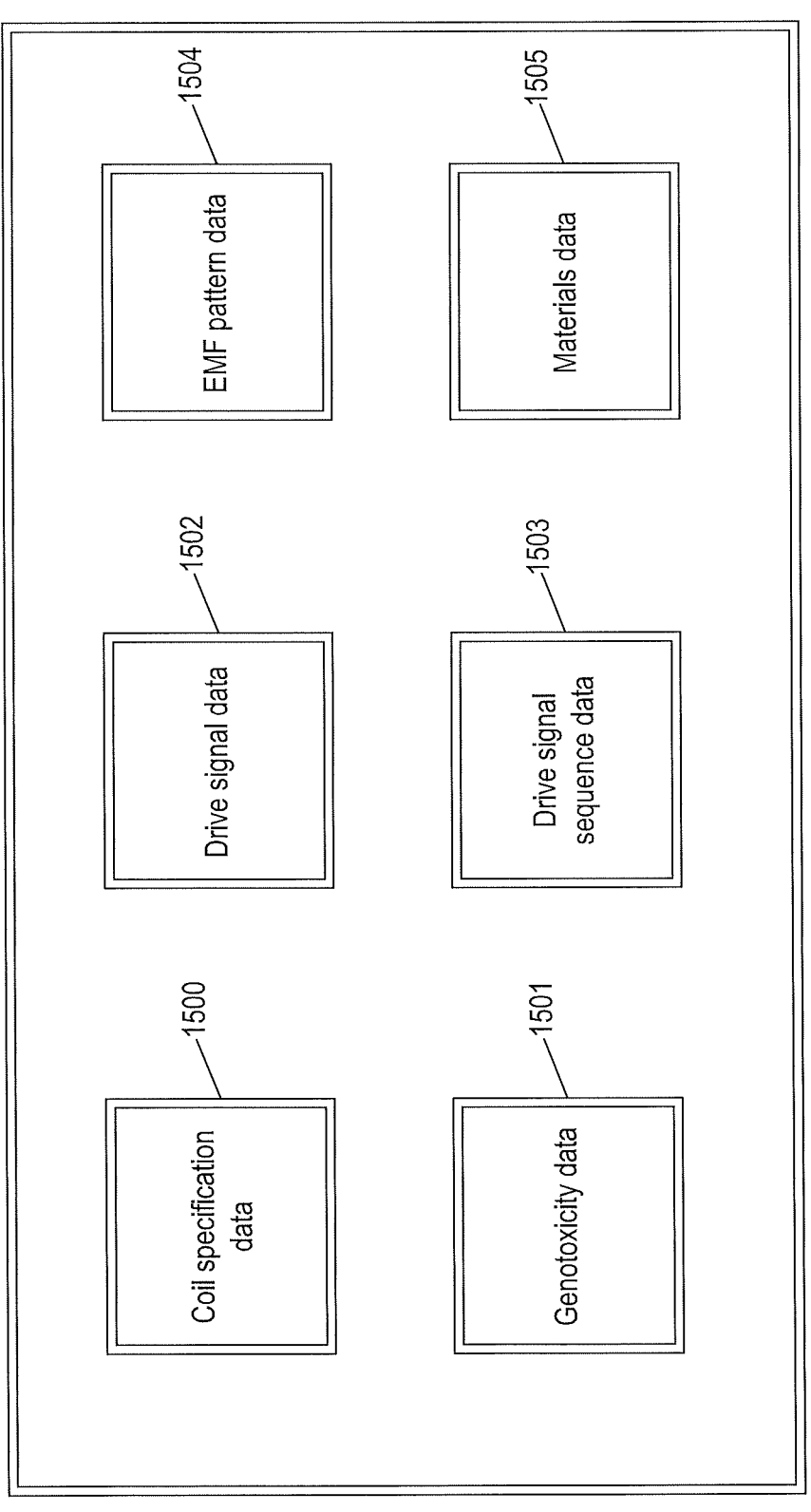
FIG. 15 herein illustrates schematically a layout of the data stored in a knowledge base of the system and apparatus of FIG. 12 herein.

Referring to FIG. 15 herein, there is illustrated schematically a layout of the knowledge base 1202. The knowledge base comprises technical data files describing various aspects of the electromagnetic patches, drive signals, and biological data.

Coil specification data 1500 comprises data describing individual coil types including coil shape, number of windings or turns, material of coil wire, diameter of coil wire, length of leads to coils, dimensions of coils including maximum width, depth and thickness, maximum power ratings of the coils, insulation types, and any other relevant information describing the coils such as manufacturer, manufacture date, cost per unit, serial number; details of the ferrite insert including: length; depth; or diameter; height; or other irregular dimensions; material specifications and performance characteristics, manufacturer/supplier.

Genotoxicity data 1501 comprises a one or a plurality of data tables, each data table describing cell type; species for the cell type; maximum safe electromagnetic dosage levels for each cell type; maximum peak electromagnetic radiation levels for each cell type; safe electromagnetic dosage levels for each cell type; safe instantaneous electromagnetic field levels of each cell type, and other relevant genotoxicity information relevant for the particular cell type. Data describing a plurality of cell types is stored.

Drive signal data 1502 comprises data describing a plurality of individual drive signal types including inflow waveforms; dc or ac; power intensity bracket (maximum) power intensity (mean) pulse width; frequency; to cycle; and other information describing individual envelope waveforms of individual drive signals. Additionally, as the waveforms are digitally synthesised, information concerning the digital pulse width, and periods and duty cycles for each way from envelope are also stored in the drive signal data 1502.

Drive signal sequence data 1503 describes a plurality of sequences of individual drive signals. The data includes information describing individual drive signal envelope (drive signal type); sequencing information describing sequences of individual drive signals, for example how many cycles of the drive signal are applied before turning the drive signal off, a wait time before applying a further drive signal, and in general a sequence data describing a plurality of individual drive signals, the wait time between the drive signals and the start and stop times of applying drive signals in sequence of drive signals. Data describing an overall cumulative dosage of electromagnetic field exposure for a particular drive seat signal sequence is also stored per each individual drive signal sequence.

Electromagnetic field pattern data 1504 comprises data describing the three-dimensional electric field strength surrounding a coil at various distances from the centre of the coil. The field strength information is stored as vector information giving both direction of field and intensity. Electromagnetic field data is stored for each of a plurality of coil specifications.

Materials data 1505 describes material properties of materials suitable for electromagnetic patch manufacture. The materials data includes data describing the material itself (for example acrylic, plastics material, specific plastics material type; hardness; flexibility; resilience; colour; material thicknesses; thermosetting properties; melting points; material bonding properties; compatibility with other materials; durability; manufacturer; product type serial number; manufacture dates and batch number; and any other data describing the material which is useful for verifying the source of the material, its suitability for medical use, and for manufacture of an electrostimulation device e.g. a patch or bespoke dental applicator (e.g. dental piece or mouthguard) from the material.

In addition, the knowledge base also comprises confidential patient data, for example an individual's age, date of birth, and characteristic of the treatment area e.g. dimensions.

Verification of Drive Unit and Electrostimulation Device

The term electrostimulation device is used interchangeably with the term electromagnetic device. Each electrostimulation (electromagnetic) device may be for example a patch or a dental applicator and is custom-made for a specific user and has applied to it a unique identifier, preferably identifying the individual device itself, or alternatively by an identifier which identifies a unique type of electromagnetic patch/electrostimulation device, where there may be one or more individual devices of the same type. In either case, either an individual device type with several instances, or each individual device itself (each device being unique) is uniquely identified for a unique individual subject user.

Each subject user may have more than one individual electromagnetic patch/electrostimulation device. For example a user may have a first-electromagnetic patch or a first electromagnetic patch type for a first tissue region of that user, for example the lower jaw, and a second electromagnetic patch or second electromagnetic patch type, for a second tissue region of the individual user.

Each individual device/patch or device/patch type designed and manufactured for a specific user has an identification means to uniquely identify the individual device/patch or patch type. The drive unit receives data describing a drive signal and/or data describing a drive signal sequence comprising a plurality of the individual drive signals delivered in a particular sequence. The drive signal data and drive signal sequence are each uniquely identified for a particular subject user and a particular tissue region of that individual subject user to be treated.

Each individual device/patch may be identified using an individual patch code, for example:

Device/Patch code: DA78945fGH78

Each individual drive signal and/or drive signal sequence may have a drive signal code, or a drive signal sequence code as appropriate, for example as follows:

Drive signal code: DER8947@67Yt

Drive signal sequence code: DFt67833998.

To match the individual drive signal and/or drive signal sequence to the individual device/patch requires matching the device/patch code to the drive signal code or drive signal sequence code. This can be achieved either by providing the electromagnetic patch code to the drive unit along with the drive signal code and drive signal sequence code, by the drive unit interrogating the identifier device on the electromagnetic patch to read the electromagnetic patch code, and then the drive unit locally comparing the patch code read from the electromagnetic patch with the patch code which was received with the drive signal code and/or the drive signal sequence codes and comparing the read patch code with the pre-stored received patch code. If the two device/patch codes match, this indicates that the electromagnetic patch is the correct patch for the receipt drive signal/or drive signal sequence, and the drive unit enables itself to supply the drive signal and/or drive signal sequence to the electromagnetic patch/electrostimulation device which has been correctly verified as being the correct patch signals.

On the other hand, if the device/patch code read of the electromagnetic patch by the drive unit does not match the pre-stored patch code received with drive signals and/or drive signal sequences, the drive unit cannot verify that the read patch is the correct patch for those drive signals and/or drive signal sequences, and the drive signal and/or drive signal sequence is disabled, i.e. is not supplied to that electromagnetic patch.

In an alternative method, the drive unit does not receive an authorised electromagnetic patch code when it receives the drive signal data and/or drive signal sequence data. Rather, when the electromagnetic patch is connected to the drive unit, the drive unit reads the identifier code (electromagnetic patch code) from the identification device electromagnetic patch. The drive unit sends the drive signal code and/or the drive signal sequence code to the knowledge centre 1202, or to the custom manufacturing facility 1203, at which a database is stored matching the individual subject user to an individual electromagnetic patch or patch type, and the drive signals and drive signal sequences for that electromagnetic patch, together with the identification codes for the patch (patch identification code) drive signals (drive signal identification codes), and drive signal sequence (drive signal sequence identification code). The manufacturing facility 1203 or knowledge centre 1202 compares the received read electromagnetic patch identification code from the drive unit, together with the drive signal identification code and/or drive signal sequence code, compares those codes with each other and verifies whether the patch identification code is the correct one for the drive signal identification code and/or drive signal sequence identification code received from the drive unit. If the patch code is the correct code that drive signal and/or drive signal sequence, then the manufacturing facility or knowledge centre supplies and enablement code or signal which enables the drive unit to use those drive signals and/or drive signal sequence with the electromagnetic patch having that patch code. It will be readily understood that there is a single centrally accessible database which may be interrogated at either the manufacturing facility 1203, in a clinical setting or implemented at any other location which has access to the database.

As described herein above, verification that the electromagnetic patch correct one for the particular drives/drive signal sequence received by the drive unit can be done locally in the drive unit itself, or drive unit can refer to the knowledge centre or manufacturing centre to receive confirmation that the electromagnetic patch is the correct one for the drive signals and/or drive signal sequences received by the drive unit.

Figure 16:
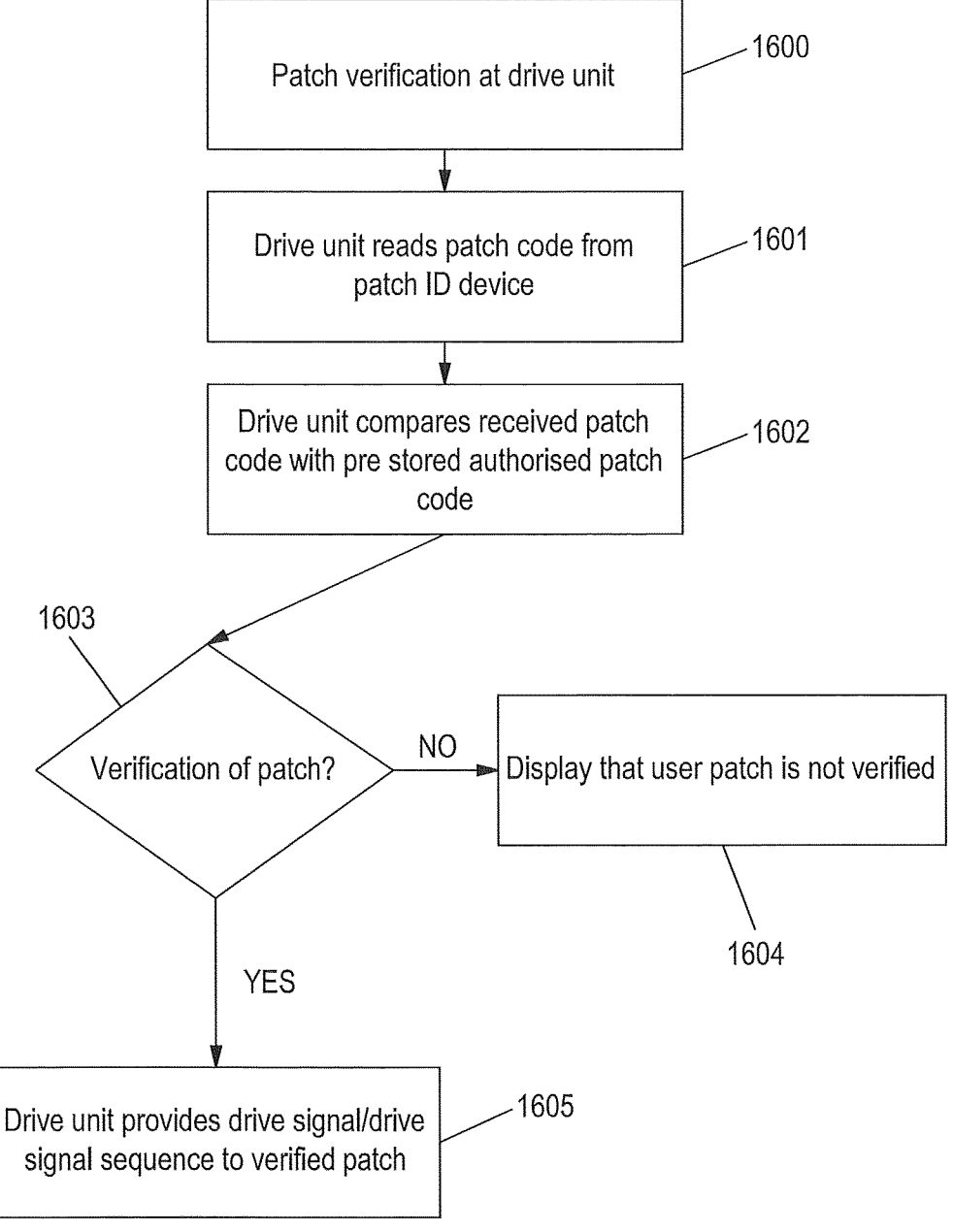
FIG. 16 herein illustrates schematically a first specific process for verification of an electromagnetic patch to the drive unit.

Referring to FIG. 16 herein, there is illustrated schematically process steps for device/patch verification 1600 at the drive unit itself, to ensure that the drive signals received by the drive unit and/or the drive signal sequence received by the drive unit is used with the correct patch for the correct subject user.

For simplicity the process is shown for patch verification 1600 but it will be understood that the same process is applied for electrostimulation device identification. In process 1601, the drive unit reads the patch code from the patch identification device. In process 1602, the drive unit compares the received patch code with a pre-programmed authorised patch code which has been received along with the drive signal data and/or drive signal sequence data. The authorised patch code data is linked with the drive signal data and/or drive signal sequence data in a message received from the knowledge centre and/or manufacturing centre, so that the authorised patch code, the drive signal code and the drive signal sequence code are uniquely linked to each other.

In process 1603, the drive unit compares the patch identification code read from the electromagnetic patch which has been connected to the drive unit with the authorised patch code received from the knowledge centre or manufacturing centre. If the codes do not match, the patch is not verified and is not authorised for use with the store drive signals, in which case the drive unit may display a signal to the user that the patch is not verified in process 1604. If in process 1603 the patch code read from the electromagnetic patch connected to the drive unit does match the authorised patch code, then process 1603 of the drive unit may display a signal or information on the smart device to alert a user that the electromagnetic patch is the correct patch for the received drive signal and/or drive signal sequence, and then they provide the drive signal and for several drive signal sequence to the electromagnetic patch. Preferably, the smart device talks to the database.

Figure 17:
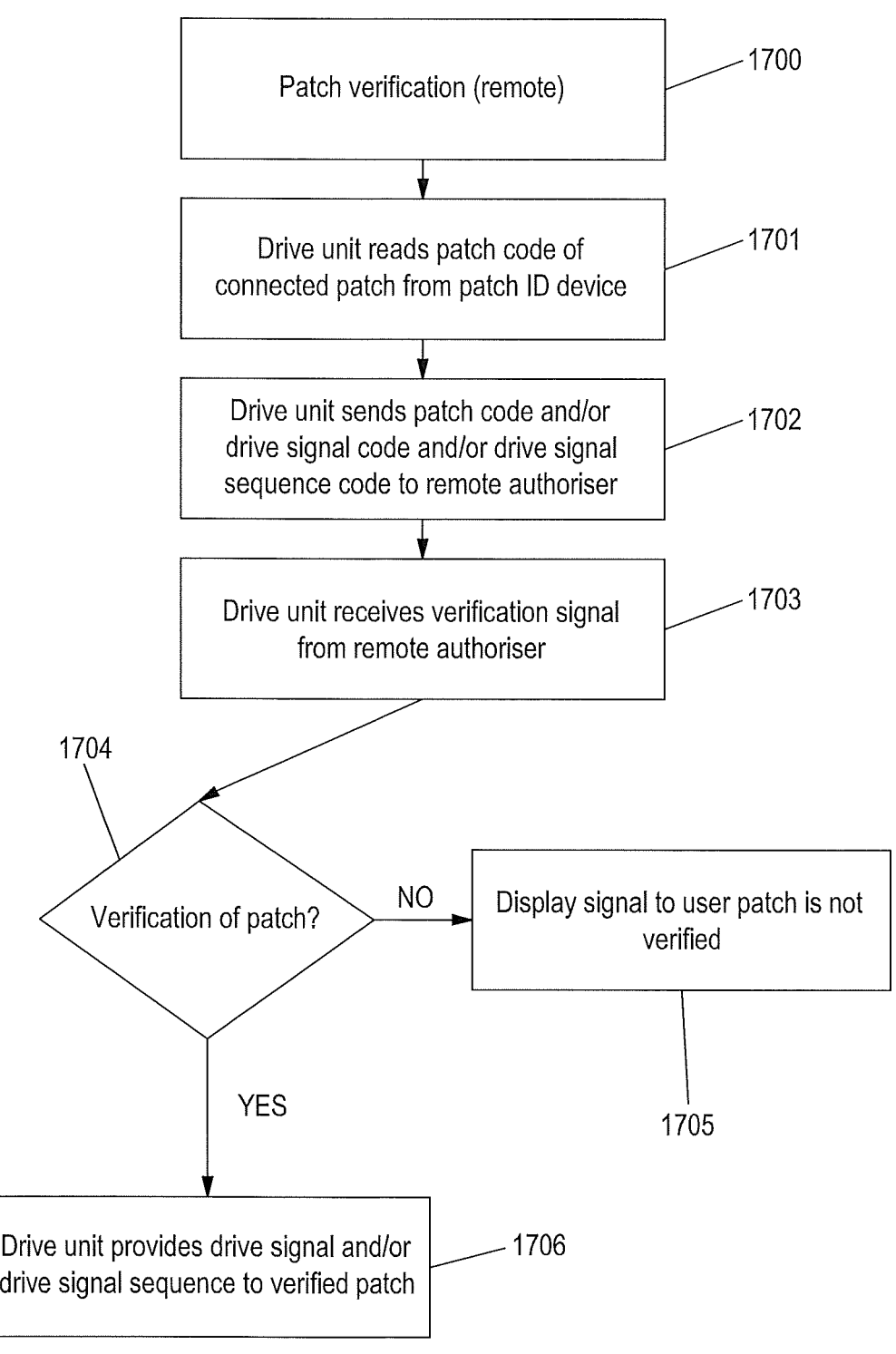
FIG. 17 herein illustrates schematically a second specific process for verification of an electromagnetic patch to the drive unit.

Referring to FIG. 17 herein, there is illustrated schematically a process 1700 carried out by the drive unit for verifying an electromagnetic patch which has been connected to the drive unit using a remote verification procedure.

In process 1701, the drive unit reads the patch identification code of the electromagnetic patch connected to the drive unit from the identification device on that patch. In process 1702, the drive unit sends the patch code together to the manufacturing centre or knowledge centre which acts as a remote authoriser for the use of that electromagnetic patch.

Where the drive unit has already received a drive signal and/or drive signal sequence from the knowledge centre or manufacturing centre and that is stored in the data storage device of the drive unit, the drive unit sends the signal identification code and/or the drive signal sequence identification code to the remote authoriser (knowledge centre or manufacturing centre) together with the patch identification code which has been read from the electromagnetic patch.

At the knowledge centre or manufacturing centre as appropriate, acting as authoriser, an authorisation module compares the received patch identification code with the received drive signal identification code and/or with the received drive signal sequence identification code and sends a verification signal to the drive unit in process 1703.

If the authorisation module determines that the codes match that is if the particular drive signal and/or drive signal sequence is the correct drive signal and/or drive signal sequence for that particular electromagnetic patch, the verification signal verifies that the electromagnetic authorised for use.

On the other hand, if the remote authorisation unit determines that the patch identifier code received from the drive unit does not match the drive signal data identification code and/or the drive signal sequence identification received from the drive unit, then verification fails 1705 and a signal is displayed to alert the user that verification has not been successful. The drive unit prohibits supply of the drive signal and/or drive signal sequence to the electromagnetic patch.

If the drive unit has not yet received drive signal data or drive signal sequence data, in process 1702, only the patch identification code is sent from the drive signal to the authorisation module remotely. The authorisation module then looks up the correct drive signal data and/or drive signal sequence data for that particular electromagnetic patch and delivers that corresponding drive signal data and/or drive signal sequence data to the drive unit together with a verification code verifying that the patch code and the drive signal identification code and/or drive signal sequence identification code are consistent for use with each other.

The drive unit then verifies the patch in process 1706 for use with the received drive signal data and/or drive signal sequence data, and provides drive signals and/or drive signal sequences to the patch, as well as indicating with an identification signal or LED message that the patch is authorised for use.

Verification of Correct Subject User and Prescription

The above patch verification procedure described with reference to FIGS. 16 and 17 verifies that the patch and the drive signals/drive signal sequence are correctly matched to each other. The drive unit will only operate with the correct patch/drive unit pairing.

Preventing a particular subject user using the wrong patch altogether can be effected as follows. Firstly, because the electromagnetic patch is of a shape specific to a particular user, and specific to a particular body region of the user they may recognise that the patch is of the incorrect shape and doesn't fit. However to prevent a subject user from using the patch anyway, a clinician or medical practitioner, or the subject user themselves may enter a prescription code into the drive unit, or into an intermediary device such as a smart phone app which connects with the drive unit wirelessly.

The prescription code may be provided in writing on the electromagnetic patch itself, on a detachable tag on the applicator or on its packaging together with written information including the subject user's name, and information describing a particular prescription, for example "Mr Abrahms, upper jaw. Use between Aug. 24, 2018 and August 31, twice daily"

"Prescription code FGt784GH672@98"

This may provide a further level of authentication, in that the clinician, medical practitioner or subject user may realise that the device is not intended for them if it does not have their name on it.

If the user enters an incorrect prescription code, that is, a prescription code which does not match the drive signal identification code and/or drive signal sequence identification code, then even if the electromagnetic patch code itself matches the drive signal identification code and/or drive signal sequence identification code, the drive unit will not provide the drive signal and may display an error message.

Communication Between the Drive Unit and the Intermediary Communication Device

In the embodiments described herein, the intermediary communication device between the drive unit and the knowledge centre and/or manufacturing facility is preferably an application programme on a smartphone, tablet or like device 1205.

The intermediary communications device may operate to accept the prescription code manually entered by the subject user, or a medical professional, and may communicate the prescription code to the drive unit via a wireless link, for example Bluetooth or Wi-Fi.

The intermediary communications device may also act as an Internet portal, communicating wirelessly with the drive unit for passage of the patch code, drive signal identifier code, drive signal sequence identifier code, drive signal data, and drive signal sequence data between the drive unit and the remote knowledge centre and/or manufacturing facility.

Dosage Programme

In the general case treatment programmes for individual subjects may operate on a daily, weekly or monthly or over any other specified treatment period with sub cycles within the overall treatment period and the treatment programmes being fully customisable and programmable. For example, the device may apply treatment for two, four or six hours per day, or any other time period between 0 and 24 hours within each day, as selected by medical practitioner or operator of the apparatus. The periods of operation may be intermittent or continuous within a daily 24 hour period.

In the general case, the treatment programmes may be fully customisable and programmable to have any electromagnetic power intensity within the range 0 to 5 mT for any duration and on any cycle of repetition during a 24-hour period.

As non-limiting examples only, a treatment programme may specify two hours per day at an intensity of 1 mT, with the drive signal on a 50% on/off cycle within the two hour period.

As another non-limiting example, another treatment programme may specify an intensity of 1.0 mT over a 4 hour period with the electromagnetic field being applied continuously throughout that four hour period.

As yet another non-limiting example, a third treatment programme may specify within a 24-hour period, 2 hours of treatment between 08:00 and 10:00 on a continuous 1 mT intensity followed by a further period of energisation between 16:00 and 18:00 at a 50% on/off cycle with a period of 5 minutes at an intensity of 1 mT.

There may be intermittent operation within an "on" treatment period. For example, within a two hour treatment session during a 24-hour daily cycle, the electromagnetic field may be cycled on and off for alternating energisation and de-energisation periods within the treatment session, so that the electromagnetic field is turned on for (for example) a first five-minute period, then turned off for a second five minutes period, then turned on again for a third five minutes period and so on throughout the two hour treatment session.

The two-hour treatment session may be preceded and/or followed by rest periods, during which the electromagnetic field is not generated, until there is another treatment session within the same daily cycle.

In other treatment programmes, during a treatment session the electromagnetic field may be constantly on, that is, not cycled across on/off energisation/de-energisation periods.

The following parameters of a treatment programme are fully customisable and programmable to suit an individual subject to user:

Number of days of treatment (overall treatment period)

For each individual treatment session within a treatment period:

Start time of treatment session;

End time of treatment session;

Power/intensity;

On/off or continuous application of signal during treatment session;

Ratio of on/off as a % a treatment session;

Specify times on & times off of signal within a treatment session e.g. 5 minutes on followed by 5 minutes off;

More than one treatment session can be applied per day.

It will be understood that treatment programmes for individual subjects may operate on a daily, weekly or monthly or over any other specified treatment period with sub cycles within the overall treatment period and the treatment programmes being fully customisable and programmable. For example, the device may apply treatment for two, four or six hours per day, or any other time period between 0 and 24 hours within each day, as selected by medical practitioner or operator of the apparatus. The periods of operation may be intermittent or continuous within a daily 24 hour period. Intermittent can be any combination and duration of on/off cycles, e.g. 1 minute on/1 minute off, 5 minutes on/5 minutes off, 1 minute on/5 minutes off, 5 minutes on/3 minutes off etc.

In the general case, any number of treatment sessions may be specified on any day of the treatment period, and the start time and stop time of each treatment session are customisable and can be predetermined. Within each treatment session the time on and time off for intermittent energised/de-energised periods of the electromagnetic field over which the drive signal is applied are programmable and customisable, as is the maximum intensity of the signal during each time on. In addition the device includes a "hold-off period", whereby the device is inoperable for set period of time e.g. 4 hours between the end of one treatment session and another to prevent the user from running multiple treatment sessions back to back. For example if a treatment session is finished at 23:45 on day 1, a further treatment session cannot be initiated on day 2 until 03:45 i.e. when the 4 hour minimum "hold-off period" has elapsed.

For example, the EMF signal may be constant or intermittent and may operate the defined periods in any given 24 hours, e.g. two, four, six or eight hours etc.

Figure 18:
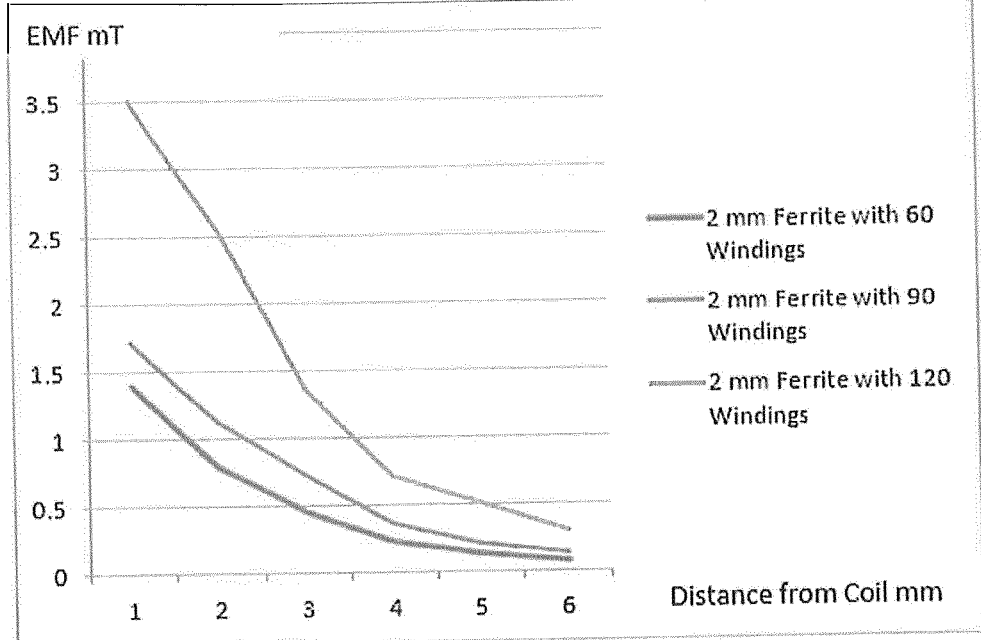
FIG. 18 herein illustrates schematically a set of data curves describing the power relationship against distance at various positions on a line passing centrally through a coil in a direction perpendicular to a main plane of the coil, for 3 different coils having different numbers of windings.

Referring to FIG. 18 herein, there is illustrated schematically a plot of electromagnetic field strength measured in mT against distance from a coil in a direction perpendicular to a main plane of the windings of the coil, for 3 types of ferrite coil having circular windings with different numbers of turns or windings. The data is given for coils having 60, 90 and 120 windings respectively. All coils are substantially identical, apart from the number of windings of the coil.

As seen from the plot, the relationship between electromagnetic field strength and distance from the main plane of the coil is that field strength drops off according to an inverse square law relationship, the further the distance from the coil. Electromagnetic field strength decreases with the square of the distance from the main plane of the electromagnetic coil.

As shown in FIG. 18, for the coil having 120 windings, the power level immediately adjacent to the coil, within 1 mm of the windings is at a potentially dangerous level, giving genotoxic effect. Hence that particular coil driven with a drive current giving those levels of electromagnetic field strength could not be placed safely within 1 mm of cellular tissue.

The knowledge base provides data describing the electromagnetic field strengths of a plurality of different coils with different numbers of windings under different drive signal conditions.

By providing data describing a plurality of different coil types and drive signal types, the power delivered to the tissue region can be adjusted either by selection of coil type and/or by selection of drive signal type. The power can be adjusted both electronically and by using coils of different numbers of windings. If a coil having a relatively larger number of windings which may produce a potentially dangerous genotoxic level of electromagnetic field strength needs to be used, for example because that coil is larger and is more suitable for a larger subject user, the level of electro-magnetic field strength can be reduced below genotoxic levels by adjustment of the drive signal for that coil. This gives an important advantage over prior art devices which use a single drive signal type and in which there is no variation of drive signal and in which high and potentially genotoxic levels of electromagnetic field need to be generated to bridge the gap between the coil and the target tissue region.

Coils having a larger number of windings generally cover a larger area than a coil with a small number of windings. Therefore the size of coil is related to the number of windings of the. Larger coils with more windings are generally used for someone with a relatively larger anatomical feature, such as a larger mouth or teeth. Similarly, coils with fewer windings are relatively smaller and may be easier to fit into a mouthpiece designed for a smaller mouth or smaller jaw area of a smaller subject.

Manufacture of Electromagnetic Patches

There will now be described a method of manufacturing electromagnetic patches in the manufacturing process 1400, including methods for placing the EMF generating coils at the target treatment location. In the examples described, dental electromagnetic patches are manufactured.

The concept of encapsulating coils and the attachment cable in a flexible substrate material is the optimum method to deliver the EMF signal in the target area, in terms of proximity, accuracy and comfort for the user.

One outline technique for their manufacture is to vacuum form an ethylene vinyl acetate (EVA) sheet over a model of the subject's unique dentition, obtained either by impression and casting of a plaster model or by 3d scanning and 3d printing.

The coil or coils are placed at the target point(s) by reference to a radiograph(s) and a prescription from a dental Clinician and by reference to the knowledge and design database.

Once the connecting cable has been routed, a second EVA sheet is subsequently vacuum formed onto the first encapsulating the coils and attachment cable in a sealed unit.

Any material that can be vacuum formed and is certified for dental application may be substituted for EVA.

Equally EVA or any suitable material certified for dental application may be formed using pressure.

An enhancement of this technique is to create both the inner and outer "moulded sheet" by 3d printing of a suitable material certified for dental application in a two-step process.

3d printing can be used to encapsulate both coils and attachment cable in a one step process.

However the technique(s) described above are not the only way that the EMF signal can be delivered to the target site.

The following methods are alternatives:

Acrylic Framework.

Figure 19:
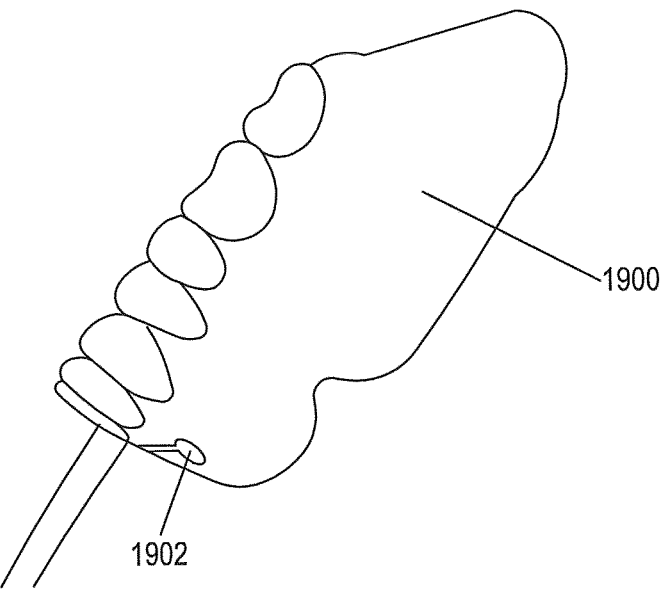
FIG. 19 herein illustrates schematically a first electromagnetic patch in the form of a prosthetic mouthpiece in view from one side.
Figure 20:
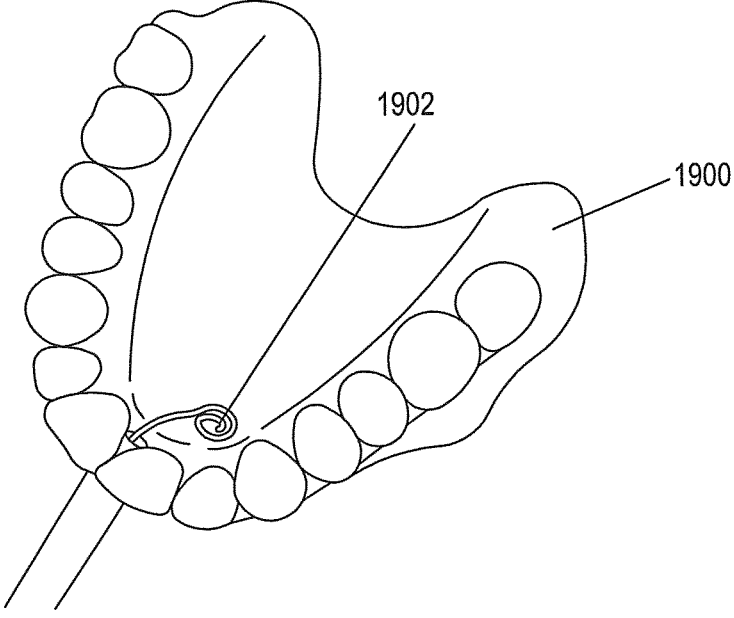
FIG. 20 herein illustrates schematically the first electromagnetic patch in view from underneath.
Figure 21:
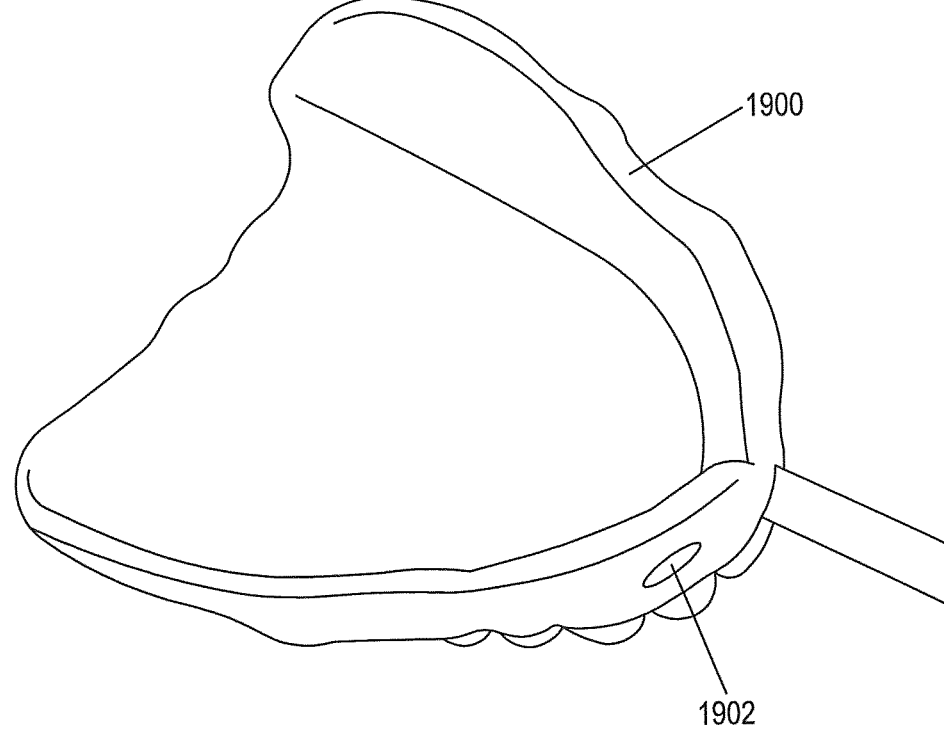
FIG. 21 herein illustrates schematically the first electromagnetic patch in view from above.

Referring to FIGS. 19 to 21 herein, there are illustrated 3 separate views of an acrylic or suitable thermoplastic framework prosthetic 1900. In the example shown, the acrylic framework prosthetic comprises an acrylic moulding in the shape of a subject's upper palate and upper dentition. Embedded in the acrylic are one or more electromagnetic coils 1902.

Using a model of the subject's unique dentition, obtained either by impression and casting of a plaster model or by 3d scanning and 3d printing, an acrylic or suitable thermoplastic framework similar to a prosthetic denture can be constructed.

Using one or more radiographs and a prescription from a dental clinician and by reference to the knowledge and design database, one or more hole(s) are drilled for the placement of a coil(s) at the treatment site. The coil(s) are secured by, and wiring including the attachment cable is routed by, the application of overlaying acrylic material. The coil(s) and wiring/attachment cable must be fully encased, so as to be isolated from contact with any tissues.

In some applications the coil(s), wires and cable attachment can be incorporated during the manufacture of the framework.

The acrylic or suitable thermoplastic frame work can be cured by any method applicable to the acrylic material used, including but not exclusively, heat, chemical (cold cure) or light.

The acrylic or suitable thermoplastic framework technique can include any material used for the manufacture of flexible dentures.

Orthodontic Framework.

Figure 22:
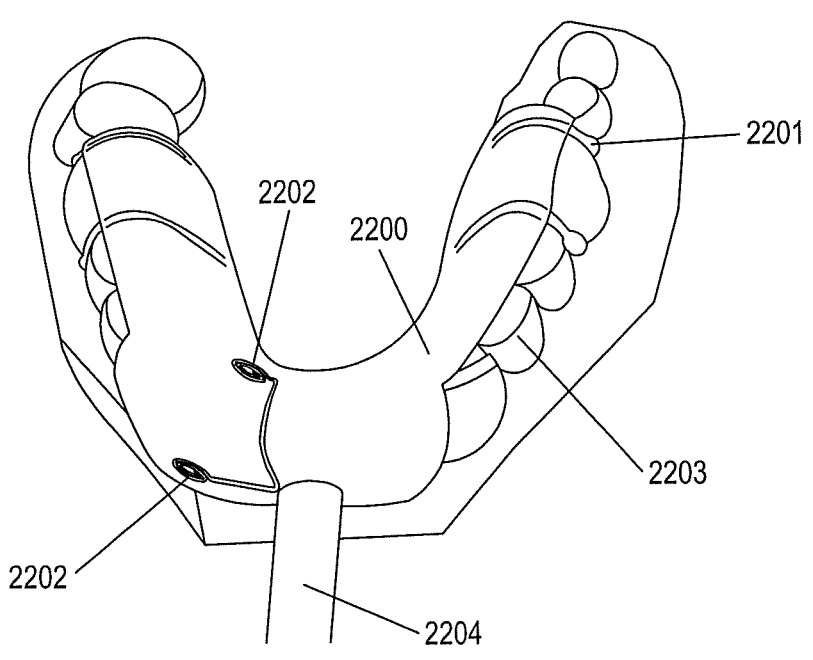
FIG. 22 illustrates schematically a second electromagnetic patch fitted to a three-dimensional model of a subject's body portion.
Figure 23:
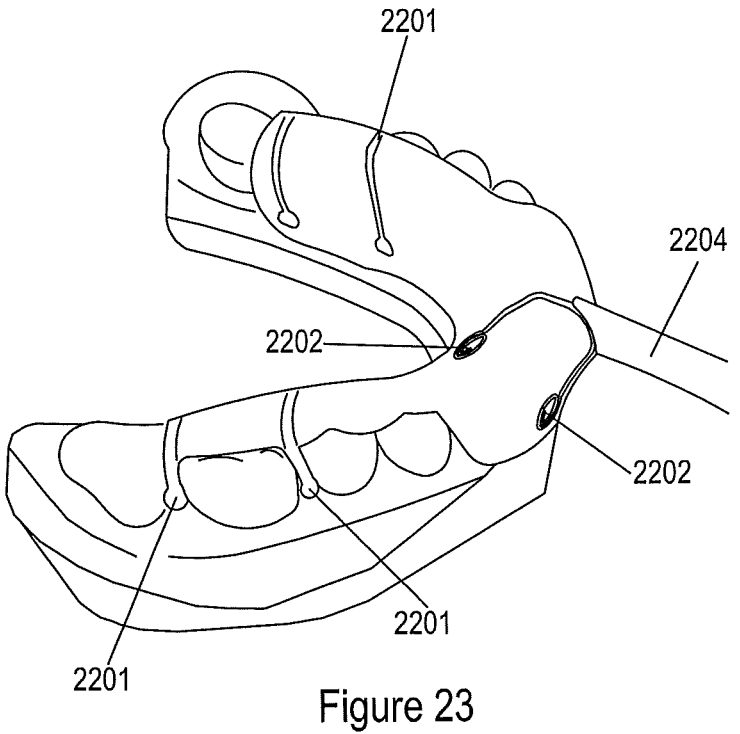
FIG. 23 illustrates schematically the second electromagnetic patch fitted to a three-dimensional model of a subject's body portion, from a different viewpoint.
Figure 24:
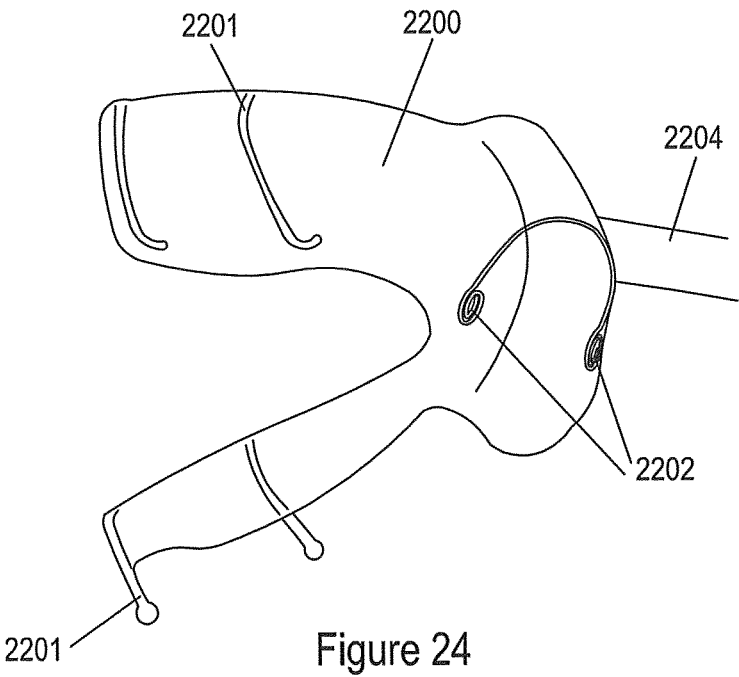
FIG. 24 illustrates schematically the second electromagnetic patch removed from the three-dimensional model of the socket body portion in view from one side and above.

Referring to FIGS. 22 to 24 herein, there is illustrated schematically electromagnetic stimulation devices/patches manufactured into the shape of an orthodontic framework. In FIGS. 19 and 20, the electromagnetic patch is shown formed on the orthodontic framework. In FIG. 24, the electromagnetic patch is shown detached from the orthodontic framework, having regions of acrylic moulding 2200 in which one or more electromagnetic coils 2202 are mounted and metal clips 2201 arranged to affix the partial mouth piece over the patient's teeth 2203. The mouthpiece being connected to and electrical connector lead 2204 preferably attached to the front incisal edge of the device which supplies a drive signal to each of the electrostimulation coils 2202 to apply an electrical signal to the coils.

Using a model of the patient's unique dentition, obtained either by impression and casting of a plaster model or by 3d scanning and 3d printing, an orthodontic framework similar to an orthodontic appliance can be constructed. This may include clasps if appropriate.

Using a radiograph(s) and prescription from a dental clinician and by reference to the knowledge and design database, coil(s) are placed at the treatment site. The coil(s) are secured by, and wiring including attachment cable is routed by, the application of overlaying orthodontic resin. The coil(s) and wiring/attachment cable must be fully encased, so isolated from contact with any tissues.

In some applications the coil(s), wires and cable attachment can be incorporated during the manufacture of the framework.

The orthodontic framework can be cured by any method applicable to the resin material used.

Metal Framework.

Figure 25:
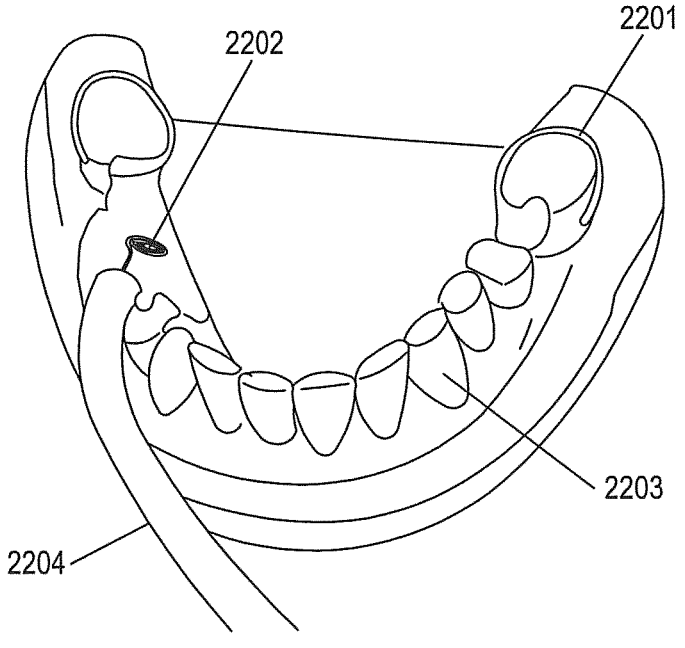
FIG. 25 illustrates schematically a third electromagnetic patch fitted to a three-dimensional model of a subject's body portion.
Figure 26:
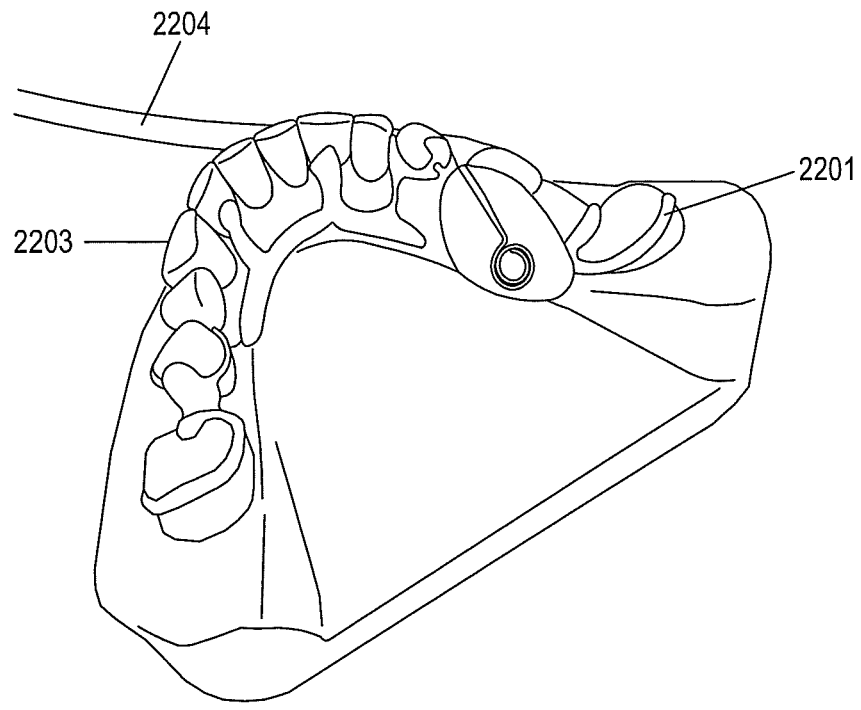
FIG. 26 illustrates schematically the third electromagnetic patch fitted to said three-dimensional model of a subject's body portion from an alternative viewpoint.
Figure 27:
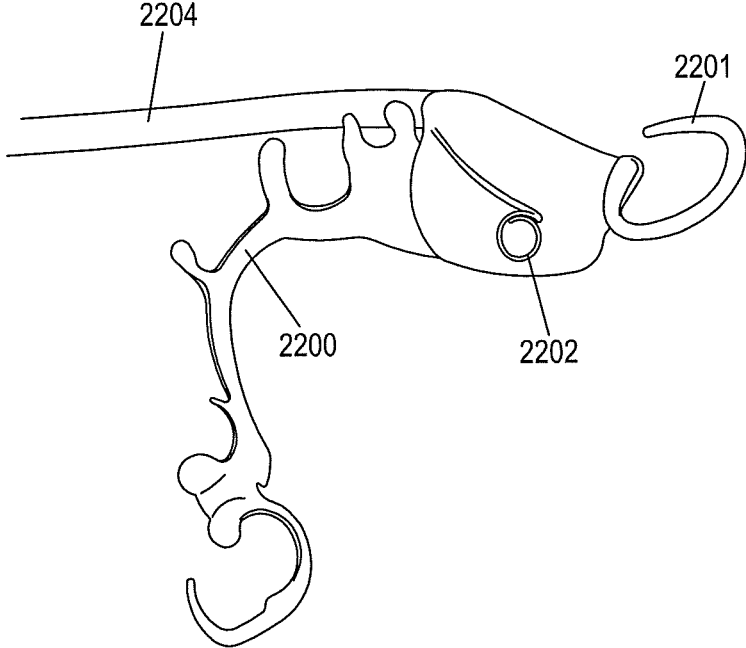
FIG. 27 herein illustrates schematically the third electromagnetic patch detached from the three-dimensional model of the subject's body portion.

Referring to FIGS. 25 to 27 herein, there is illustrated schematically a bespoke electromagnetic stimulation device/mouthpiece having a metal framework 2201. In FIGS. 22, 23 and 25, a metal framework is fitted to a three-dimensional model of the patient's mouth. In FIGS. 24 and 27, the metal framework is shown detached from the model of the patient's mouth.

Using a model of the patient's unique dentition, obtained either by impression and casting of a plaster model or by 3d scanning and 3d printing, a metal framework similar to a metal prosthetic denture can be constructed. Construction material may include, but will not be confined to Chrome Cobalt, Vitalium or any appropriate metal or metal alloy approved for dental application.

Using one or more radiographs and prescription from a dental clinician and by reference to the knowledge and design database, one or more coil(s) are placed at the treatment site. The coil(s) are secured by, and wiring including attachment cable is routed by, application of overlaying acrylic material. The coil(s) and wiring/attachment cable must be fully encased, so isolated from contacting any tissues.

The acrylic material can be cured by any method applicable to the type used, including but not exclusively, heat, chemical (cold cure) or light. This includes any material used for the manufacture of flexible dentures.

Alternatively, the coil(s) are secured by, and wiring including attachment cable is routed by, the application of overlaying orthodontic resin. The coil(s) and wiring/attachment cable must be fully encased, so isolated from contact with any tissues.

The orthodontic material can be cured by any method applicable to the resin material used.

Stabilisation/Structural Retainer

There may be a number of situations where the treatment area may need stabilisation beyond the direct application of the EMF treatment. One particular example might be where periodontal disease has resulted in bone/tissue loss around a tooth or group of teeth. In such a situation the teeth may be described as 'mobile' or 'loose'. Similarly an accident or other trauma may create the same situation.

As with other situations where structural integrity is lost (e.g. broken/damaged/resorbed bone), it may necessary to stabilise the treatment area to avoid movement in order for healing to occur.

In the oral cavity this can be achieved by the use of a 'soft' occlusal retainer or 'hard' Essix or Trutain retainer. In both 'soft' and 'hard' cases the retainer can cover the full arch, or a quadrant or individual teeth, depending on the individual patient. It would most likely be the case that the retainer is worn for 24 hours, except when EMF treatment is being applied, where the treatment patch itself affords stability.

Figure 28:
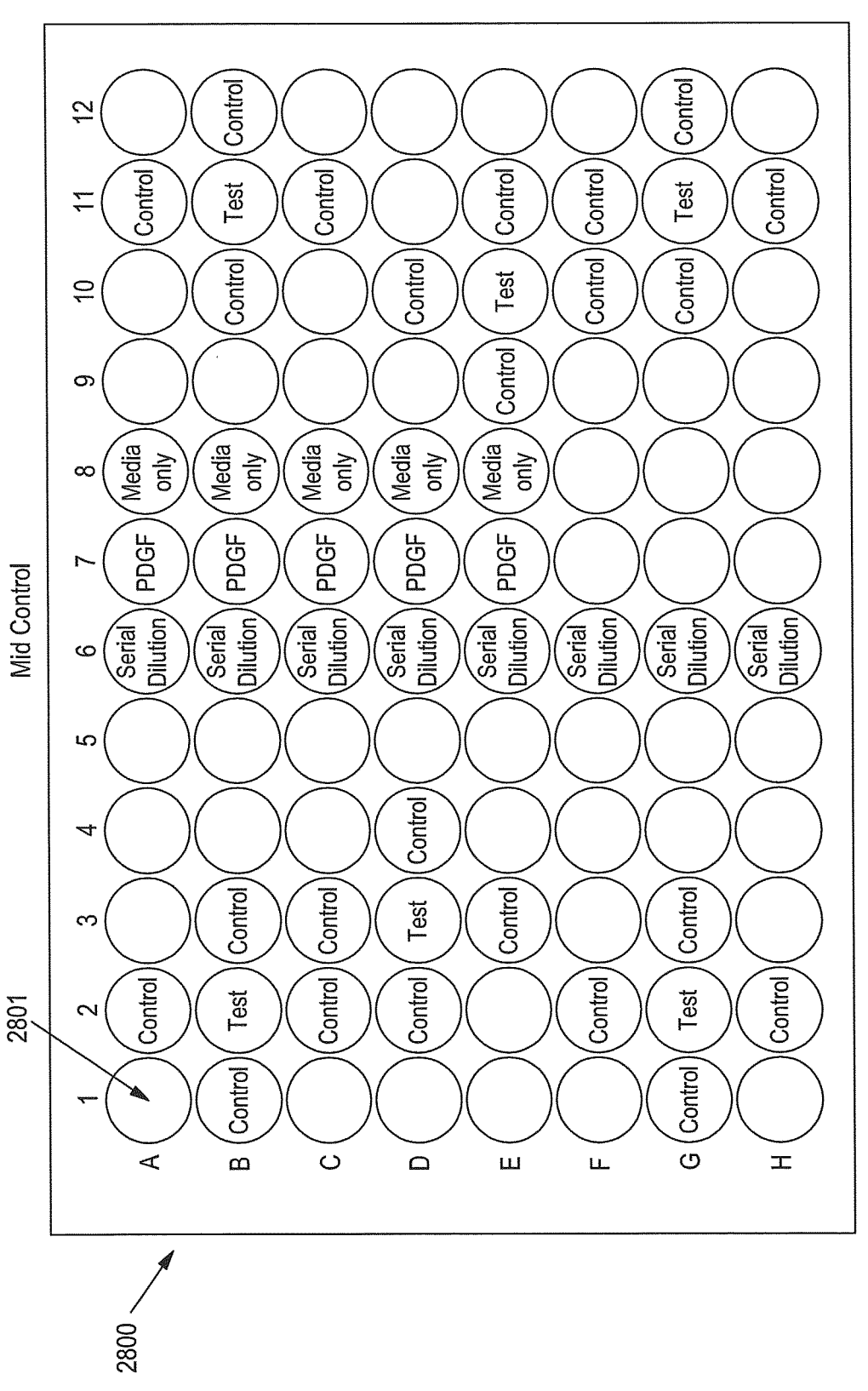

Experimental Results and Characterisation of Drive Signals and Drive Signal Sequences Referring to FIG. 28 herein, there is illustrated a multi-well plate 2800 in view from above having individual test wells 2801, as used in a third cell proliferation assay in which cell proliferation is measured under conditions of electro stimulation of different overall drive signal envelope frequencies.

FIGS. 29 to 36 herein present the experimental set up used to measured data for cell proliferation and genotoxicity in cell cultures exposed to electromagnetic fields of different field strengths, frequencies, drive signal types and drive signal sequences. A probe 2900 of a Gauss meter 2901 is used to read the electromagnetic stimulation provided to cells in a multi-well plate 2902 by an electrostimulation device according to the present invention powered by a drive unit 2903.

FIG. 29 herein illustrates schematically a photographic test kit comprising a 96 well plate and a Gauss meter.

FIG. 30 herein illustrates schematically the 96 well plate 2902 and Gauss meter probe 2900 in use for testing electromagnetic radiation levels in a test well.

FIG. 31 herein illustrates schematically in graphical form a plot of percentage cell proliferation for cells exposed to AC electromagnetic stimulation at a frequencies of 7.6 Hz at different duty cycles of 1/1 and 5/5 and a continuous signal. In each case the proliferation is compared to the control column immediately to its right and set to 100%. The asterisk indicates that the level of proliferation is statistically significant.

FIG. 32 herein illustrates schematically in graphical form a plot of percentage cell proliferation for cells exposed to DC electromagnetic stimulation at a frequencies of 7.0 Hz at different duty cycles of 1/1 and 5/5 and a continuous signal. In each case the proliferation is compared to the control column immediately to its right and set to 100%. The asterisk indicates that the level of proliferation is statistically significant.

FIG. 33 herein illustrates a genotoxicity assay technique by reference to a positive (genotoxicity) and control (no genotoxicity) slides viewed using a fluorescence microscope. The positive effect was created by exposing gingiva fibroblast primary isolated cells to etoposide 2. In the control, the gingiva fibroblast primary isolated cells were not exposed to etoposide 2. The assay technique was used to show whether cells exposed to either AC or DC electromagnetic stimulation demonstrated genotoxicity compared to cells that received no electromagnetic stimulation.

FIG. 34 herein illustrates schematically determination of safe conditions for DC electromagnetic stimulation at 1 mT, 7.6 Hz, 8 hours/day at 5 minutes on/5 minutes off viewed using a fluorescence microscope. The absence of any green fluorescence indicates a complete absence of genotoxicity in the test.

FIG. 35 herein illustrates schematically determination of the safe conditions for DC electromagnetic stimulation at 1 mT, 7.6 Hz, 8 hours/day 5 minutes on 5 minutes off. The absence of any green fluorescence indicates a complete absence of genotoxicity in the test.

FIG. 36 herein illustrates genotoxicity data for cell cultures exposed to electromagnetic fields of different field strengths, frequencies, drive signal types and drive signal sequences.

Genotoxicity

The inventors set out to determine a safe treatment level for in-vitro cells by investigate whether there is any detrimental effect (DNA damage), following EMF stimulation.

To do this required a suitably sensitive test: Oxidative DNA Damage Analysis

8-Oxodeoxyguaosine (8-OxodG) is commonly used as a marker of ROS-induced DNA damage. Avidin binds with high specificity to 8-OxodG in DNA and was used in this trial to detect 8-OxodG residues in the cells. (Gharibi et al., 2014)

Materials and Methods

Stimulated human gingival fibroblasts were fixed in 4% paraformaldehyde in PBS and permeabilized with 1% Triton for 15 minutes. Between every step the cells were washed 3 times with PBS. After blocking with PBS containing 1% BSA, cells were stained with FITC-conjugated avidin (Biolegend) 5 µg/ml overnight at 4° C. Staining followed the next day with DAPI (1:1000) for 10 minutes at room temperature. The results were visualized under fluorescence microscopy.

100 µM Etoposide was used as positive control for DNA damage (Jamil et al., 2015).

Time Limiting Trial

Following several initial trials to verify the technique, the assessment trial was time limited to better reflect the conditions that would apply in a clinical setting, i.e. treatment via a patch would be for set periods of time each day. These time intervals were set at 4 or 6 or 8 hours per day as shown in FIG. 37 herein.

Under these conditions and with an EMF level of 1 mT there was zero genotoxic effect. The two examples in FIGS. 34 and 35 show the highest level of exposure for alternating current (AC) and direct current (DC) stimulation via intermittent 5 minutes on and 5 minutes off stimulation.

When the experiment was repeated with an EMF level of 1.5 mT there was a small but consistent genotoxic effect.

Safety of the Magnetic Field Associated with Intraoral Devices According to the Invention Intraoral devices of the present invention are designed to use a time-varying magnetic field to facilitate organic cell proliferation and aid oral healing e.g. following periodontal (gum) disease treatment. In consultation with a Magnetic Resonance Safety Expert, theoretical studies demonstrated that a device according to the invention having a magnetic field frequency of 7.0 Hz (sinusoidal, avoiding harmonics) having a field amplitude of 1 mT appeared very safe. At 7 Hz, the proposed 1 mT exposure generated by the device of the present invention is slightly higher than the general public reference level, but well below the occupational reference level of the International Commission for Non-Ionising Radiation Protections (ICNIRP) who have published guidelines for limiting exposure to time-varying electric and magnetic fields of 1 Hz to 100 kHz, to provide protection against all established adverse health effects.

Specific Adjustment and Verification of Safe Application

It will be apparent from the preceding methodology that each treatment patch is patient specific; as such it must accommodate unique and irregular shapes around the treatment area. Equally apparent is that the patch material is flexible, as is the patient's tissues. This means that the angle of placement and indeed the thickness of the inner material cannot be wholly predicted by modelling.

Accordingly it is important that the area of treatment is tested and an actual EMF map established. Further that the map is optimised to ensure the best coverage of EMF signal whilst ensuring that the level is within established safe limits.

This is undertaken as the final stage of the manufacturing process. To do this in practice, consider the case of a dental patch which is arguably the most complex case, although the principal applies to all patches regardless of application around the body.

Once the unit has been produced it must be orientated to give full access to the treatment field and secured with sufficient strength that it will not move, but equally will not be distorted from its normal configuration. For example it might be lightly embedded in dental putty or similar substance.

FIGS. 37, and 38 herein illustrate schematically in perspective and side view respectively, a treatment patch 3700 consisting of a pair of diametrically opposed electromagnetic coils spanning a plastic three-dimensional support 3701 receivable in a patient's mouth e.g. a bespoke mouthguard across access X₁-X₁. The support is mounted on a jig 3702 which permits movement of the device in three dimensions according to the axes illustrated in FIG. 37 and shown relative to the profile of the support 3703 in FIGS. 39*a* and 39*b*. A Gauss meter 3704 probe is attached to the jig.

The Gauss meter probe 3704 in transverse application is attached to jig 3702 to allow movement in three dimensions and for that movement to be recorded on the display unit of the Gauss meter 3705. Thus establishing a three dimensional 'EMF map'. By reference to the 'area of treatment' the positioning of the coils can be assessed. Should they be found to not "overlap" sufficiently, it may be necessary to re-position and re-manufacture the patch. This decision will be a clinical assessment by a clinician or qualified technician.

If the fit of EMF map' over 'treatment area' is considered acceptable, it might still be necessary to increase or indeed decrease the EMF level for optimisation. This can be achieved by altering the electrical power output from the generator using a software access programme. Once optimisation has been achieved the exact power settings are sent back to the main server to update the specific parameters for the patient.

This feedback loop ensures that the patient has a patch with parameters that have been optimised for use and which are verified within safe operating limits. The information must accompany the electronic unit and patch both as a written prescription and electronically embedded in the software settings.

In some cases it may be the case that the actual electronic unit is tested with the patch. However, where electronic units and patches are mass produced, it may be the case that optimisation units and patient electronic units are quality assured to ensure compliance. A regime for checking the optimisation units must be established and strictly adhered to.

It will be appreciated by the person skilled in the art that in the above described embodiments, individual technical features of one embodiment may be added to and/or substituted for individual technical features of any other embodiment described herein, and the technical features of the described embodiments may be combined in any combination or combinations of individual technical features and are not mutually exclusive of each other, in order to achieve the described technical results, effects and/or purposes.

Advantages

Specific embodiments and methods herein provide a novel solution for the production of a sinusoidal electromagnetic field wave which is distinct from previously used technology using sinusoidal electromagnetic field treatments.

Prior art technology relied on a square size signal which was smoothed electronically to produce a more rounded curve. This is effectively the technology of a DC to AC inverter.

Specific embodiments herein allow controlled and precise variation of both frequency and power, but particularly the power of an overall drive signal waveform. Drive signals can be digitally synthesised and can be custom created for a particular subject user and tissue region and tissue type by referring to data tables of optimised drive signals for particular cell types, which have been previously determined by experimentation.

The important variables are power, time and frequency, but especially power. The inventors have determined that electromagnetic fields exceeding 1 mT can cause small but detectable genotoxic like effects. Therefore in the present embodiments each electromagnetic patch applicator is manufactured specific for an individual subject user, in the case of a dental impression using either physical impression of the dental arch or by a 3-D scan of the arch and 3-D modelling or by other means as described herein above. The applicator may for example be a bespoke electromagnetic dental stimulation applicator (BEDSA).

Further, in the present system because the power can be varied with fine control to the coils the electromagnetic field can be tuned to give the optimum effect at the target tissue region while still remaining beneath genotoxic levels. A Gauss meter can be used with a three-dimensional jig to position a probe precisely in the target area to be treated. Some individual subject users will have larger anatomical features than others and so will require a different and tuned power setting. This feature is not present in known prior art devices.

REFERENCES

GHARIBI, B., FARZADI, S., GHUMAN, M. & HUGHES, F. J. 2014. Inhibition of Akt/mTOR attenuates age-related changes in mesenchymal stem cells. *Stem Cells*, 32, 2256-66.

JAMIL, S., LAM, I., MAJD, M., TSAI, S. H. & DURONIO, V. 2015. Etoposide induces cell death via mitochondrial-dependent actions of p53. *Cancer Cell Int*, 15, 79.

The invention claimed is:

1. An apparatus configured for an electromagnetic stimulation of organic cells by an electromagnetic field, said apparatus comprising:

an electromagnetic stimulation device comprising at least one electromagnetic coil;

an electrical drive unit configured for generating a drive signal for powering said at least one electromagnetic coil;

said electromagnetic stimulation device being a bespoke mouthpiece provided with a unique identifier device configured for identifying said bespoke mouthpiece electromagnetic stimulation device to said drive unit;

said electrical drive unit comprises a single socket connector, which is used alternately for connection of an external power supply or for connection of said bespoke mouthpiece electromagnetic stimulation device comprising at least one electromagnetic coil, in a manner that said external power supply and said bespoke mouthpiece electromagnetic stimulation device comprising at least one electromagnetic coil cannot be connected to the drive unit at the same time;

said electrical drive unit being provided with a radio frequency identification tag (RFID) or a microchip configured for recognizing said unique identifier device for identifying said bespoke mouthpiece electromagnetic stimulation device;

said electrical drive unit configured to supply the drive signal to said at least one electromagnetic coil when said drive unit verifies said unique identifier device, and said drive unit is disabled from supplying the drive signal to said at least one electromagnetic coil when said drive unit does not verify said unique identifier device.

2. The apparatus according to claim 1, wherein said unique identifier device comprises a device selected from the set:

an integrated circuit or a memory device storing a unique identifier data which uniquely identifies said electromagnetic stimulation device.

3. The apparatus according to claim 1, wherein the electromagnetic stimulation device comprises an electrical lead, wherein said unique identifier device is located at an opposite end of said lead to said at least one electromagnetic coil.

4. The apparatus according to claim 1, wherein said electromagnetic field generates a field strength of less than or equal to 1 milliTesla (mT) at an outer surface of said electromagnetic stimulation device, a drive frequency in the range 5.0 Hertz (Hz) to 8.0 Hz and a current in the range 50 milliampere (mA) to 1000 mA.

5. The apparatus according to claim 1, wherein said electromagnetic field generates a field strength of less than or equal to 1 milliTesla (mT) at an outer surface of said electromagnetic stimulation device, a drive frequency in the range 7.0 Hertz (Hz) to 7.6 Hz and a current in the range 50 milliampere (mA) to 1000 mA.

6. The apparatus according to claim 1, wherein the electromagnetic field is applied continuously for a period of 2 to 8 hours per day.

7. The apparatus according to claim 1, wherein the electromagnetic field is applied continuously for a period of 2, 4, 6 or 8 hours per day.

8. The apparatus according to claim 1, wherein the electromagnetic field is applied intermittently for a period of 2 to 8 hours per day.

9. The apparatus according to claim 8, wherein the electromagnetic field is applied intermittently for a period of 5 minutes then no electromagnetic field is applied for a period of 5 minutes, consecutively for a designated treatment period of 2 to 8 or 2, 4 or 6 hours per day.

10. The apparatus according to claim 1, wherein the electromagnetic field is applied intermittently for a period of 2, 4 or 6 hours per day.

11. The apparatus as claimed in claim 1, wherein said drive unit comprises:

a power storage device;

a microprocessor device;

a power circuit for providing drive current to said at least one electromagnetic coil;

a connector for connecting said drive unit to said electromagnetic stimulation device; and a communications port and a memory device or a data storage device for receiving and storing a set of signal data for implementing a programme comprising a series of one or more drive signals applied to said electromagnetic stimulation device.

* * * * *